US006971998B2

(12) United States Patent
Rosenman et al.

(10) Patent No.: US 6,971,998 B2
(45) Date of Patent: Dec. 6, 2005

(54) IMPLANT DELIVERY CATHETER SYSTEM AND METHODS FOR ITS USE

(75) Inventors: Daniel C. Rosenman, South San Francisco, CA (US); Peter A. Altman, South San Francisco, CA (US); Mark A. Lovich, South San Francisco, CA (US); Micheal A. Schwartz, South San Francisco, CA (US); Aaron J. Miller, South San Francisco, CA (US)

(73) Assignee: BioCardia, Inc., South San Francisco, CA (US)

( * ) Notice: Subject to any disclaimer, the term of this patent is extended or adjusted under 35 U.S.C. 154(b) by 32 days.

(21) Appl. No.: 10/292,667

(22) Filed: Nov. 12, 2002

(65) Prior Publication Data

US 2003/0073972 A1    Apr. 17, 2003

Related U.S. Application Data

(63) Continuation of application No. 09/543,127, filed on Apr. 5, 2000, now Pat. No. 6,478,776.

(51) Int. Cl.[7] .................... A61M 31/00; A61M 5/178
(52) U.S. Cl. .............. 604/57; 604/93.01; 604/164.1
(58) Field of Search .......................... 604/164.01, 523, 604/500, 502, 508, 164.1, 57, 93.01; 607/119–120, 607/122, 126, 127, 128

(56) References Cited

U.S. PATENT DOCUMENTS

| | | | |
|---|---|---|---|
| 3,718,512 A * | 2/1973 | Hurst | 149/2 |
| 4,003,379 A | 1/1977 | Ellinwood, Jr. | 128/260 |
| 4,146,029 A | 3/1979 | Ellinwood, Jr. | 128/260 |
| 4,181,123 A | 1/1980 | Crosby | 128/6 |
| 4,296,100 A | 10/1981 | Franco | 424/108 |
| 4,319,562 A | 3/1982 | Crosby | 128/1 R |
| 4,360,031 A | 11/1982 | White | 128/786 |
| 4,565,649 A * | 1/1986 | Vogel | 252/503 |
| 4,577,642 A | 3/1986 | Stokes | 424/425 |
| 4,606,118 A | 8/1986 | Cannon et al. | 29/825 |
| 4,634,546 A * | 1/1987 | Kalnin et al. | 252/506 |
| 4,711,251 A | 12/1987 | Stokes | 128/784 |
| 4,722,875 A * | 2/1988 | Wright | 429/103 |
| 4,797,285 A | 1/1989 | Barenholz et al. | 424/250 |
| 4,819,661 A | 4/1989 | Heil, Jr. et al. | 128/786 |
| 4,844,099 A | 7/1989 | Skalsky et al. | 128/785 |
| 4,884,567 A | 12/1989 | Elliott et al. | 128/303 R |
| 4,892,538 A | 1/1990 | Aebischer et al. | 604/891.1 |

(Continued)

OTHER PUBLICATIONS

Arzbaecher, et al., Development of An Automatic Implanted Drug Infusion System for the Management of Cardiac Arrhythmias, 76 IEEE Proc. 1204 (1991).

(Continued)

*Primary Examiner*—Nicholas D. Lucchesi
*Assistant Examiner*—Sundeep Virdi
(74) *Attorney, Agent, or Firm*—K. David Crockett, Esq.; Crockett & Crockett

(57) ABSTRACT

Catheter systems and methods for implanting helical or dart-like implants into the myocardium or other body tissue. The catheter system includes a helix for fixing the distal end of the catheter to the myocardium, an implant held by the helix, mechanisms for driving the fixation helix into the myocardium, and mechanisms for driving the implant into the myocardium, removing the fixation helix and leaving the implant behind. The implant may be coated, filled, or made of a drug or drug eluting compound, or drug delivery matrix of any composition.

3 Claims, 17 Drawing Sheets

U.S. PATENT DOCUMENTS

| | | | |
|---|---|---|---|
| 4,900,303 A | 2/1990 | Lemelson | 604/54 |
| 4,936,317 A | 6/1990 | MacGregor | 604/890.1 |
| 4,946,457 A | 8/1990 | Elliott | 606/1 |
| 4,991,578 A | 2/1991 | Cohen | 128/419 |
| 4,991,603 A | 2/1991 | Cohen et al. | 128/786 |
| 4,998,975 A | 3/1991 | Cohen et al. | 128/419 D |
| 5,002,067 A | 3/1991 | Berthelsen et al. | 128/786 |
| 5,016,640 A | 5/1991 | Ruiz | 128/658 |
| 5,030,204 A | 7/1991 | Badger et al. | 604/95 |
| 5,033,477 A | 7/1991 | Chin et al. | 128/785 |
| 5,062,829 A * | 11/1991 | Pryor et al. | 604/57 |
| 5,068,829 A * | 11/1991 | Yamaguchi et al. | 604/57 |
| 5,176,907 A | 1/1993 | Leong | 424/78.08 |
| 5,190,761 A | 3/1993 | Liburdy | 424/450 |
| 5,220,917 A | 6/1993 | Cammilli et al. | 128/419 |
| 5,236,424 A | 8/1993 | Imran | 604/280 |
| 5,244,460 A | 9/1993 | Unger et al. | 604/53 |
| 5,269,326 A | 12/1993 | Verrier | 128/642 |
| 5,283,187 A | 2/1994 | Aebischer et al. | 435/182 |
| 5,322,064 A | 6/1994 | Lundquist | 128/4 |
| 5,324,325 A | 6/1994 | Moaddeb | 607/120 |
| 5,385,148 A | 1/1995 | Lesh et al. | 128/662.06 |
| 5,387,419 A | 2/1995 | Levy et al. | 424/422 |
| 5,405,376 A | 4/1995 | Mulier et al. | 607/127 |
| 5,429,131 A | 7/1995 | Scheinman et al. | 128/642 |
| 5,431,649 A | 7/1995 | Mulier et al. | 606/41 |
| 5,447,533 A | 9/1995 | Vachon et al. | 607/120 |
| 5,496,360 A | 3/1996 | Hoffmann et al. | 607/120 |
| 5,527,344 A | 6/1996 | Arzbaecher et al. | 607/3 |
| 5,531,780 A | 7/1996 | Vachon | 607/120 |
| 5,551,427 A * | 9/1996 | Altman | 600/374 |
| 5,609,151 A | 3/1997 | Mulier et al. | 128/642 |
| 5,629,008 A * | 5/1997 | Lee | 424/426 |
| 5,634,895 A | 6/1997 | Igo et al. | 604/21 |
| 5,651,986 A | 7/1997 | Brem et al. | 424/484 |
| 5,661,133 A | 8/1997 | Leiden et al. | 514/44 |
| 5,662,689 A | 9/1997 | Elsberry et al. | 607/5 |
| 5,681,278 A | 10/1997 | Igo et al. | 604/52 |
| 5,690,682 A | 11/1997 | Buscemi et al. | 607/3 |
| 5,693,622 A | 12/1997 | Wolff et al. | 514/44 |
| 5,698,531 A | 12/1997 | Nabel et al. | 514/44 |
| 5,704,910 A | 1/1998 | Humes | 604/52 |
| 5,722,400 A | 3/1998 | Ockuly et al. | 128/642 |
| 5,773,019 A | 6/1998 | Ashton et al. | 424/423 |
| 5,782,828 A | 7/1998 | Chen et al. | 606/42 |
| 5,785,706 A | 7/1998 | Bednarek | 606/41 |
| 5,797,870 A * | 8/1998 | March et al. | 604/506 |
| 5,807,395 A | 9/1998 | Mulier et al. | 606/41 |
| 5,810,836 A | 9/1998 | Hussein et al. | 606/108 |
| 5,829,447 A | 11/1998 | Stevens et al. | 128/898 |
| 5,833,715 A | 11/1998 | Vachon et al. | 607/120 |
| 5,840,059 A | 11/1998 | March et al. | 604/53 |
| 5,945,100 A | 8/1999 | Fick | 424/93.21 |
| 5,951,585 A | 9/1999 | Cathcart et al. | 606/198 |
| 6,086,582 A | 7/2000 | Altman et al. | 606/41 |
| 6,102,887 A | 8/2000 | Altman | 604/22 |
| 6,258,119 B1 | 7/2001 | Hussein et al. | 606/108 |
| 6,450,937 B1 * | 9/2002 | Mercereau et al. | 600/7 |

OTHER PUBLICATIONS

Bloem, et al., Use fo Microprocessor Based Pacemaker to Control an Implantable Drug Delivery System, Computers in Cardiology 1 (1993).

Bloem, et al., Microprocessor Based Automatic Drug Infusion System for Treatment of Paroxysmal Atrial Fibrillation, 26S J. Electrocardiogr. 60 (1993).

Wood, et al., Feedback Control of Antiarrhythmic Agents, Molecular Interventions and Local Drug Delivery 399 (1995).

Siden, et al., Epicardial Controlled Release Verapimil Prevents Ventricular Tachycardia Episodes Induced by Acute Ischemia in a Canine Model, 19 J. Cardiovascular Pharmacology 798 (1992).

Scheinman, Supraventricular Tachyarrhythmias: Drug Therapy Versus Catheter Ablation, 17 Clinical Cardiology II-11 (1994).

CAST Investigators, The Effect of Encainide and Flecainide on Morraility in a Randomized Trial of Arrhythmia Suppression after Myocardial Infarction, 321 N. Engl. J. Med 406 (Aug. 1989).

Echt, et al., Mortality and Morbidity in Patients Receiving Encainide, Flecainide, or Placebo—The Cardiac Arrhythmia Suppression Trial, 324 N. Engl. J. Med. 781 (Mar. 199.

Lesh et al. Potential Role of 'hybrid therapy' for Atrial Fibrillation, Semin Intervent Cardiol 1997; 2:267-271.

Lazarous et al., Comparative Effects of Basic Fibroblast Growth Factor and Vascular Endothelial Growth Factor on Coronary Collateral Development and the Arterial Response to Injury, 94 Circulation 1074-1082 (Sep. 1996).

Lin et al., Expression of Recombinant Genes In Myocardium In Vivo After Direct Injection Of DNA, 82 Circulation 2217-2221 (Dec. 1990).

French et al., Direct In Vivo Gene Transfer into Porcine Myocardium using Replication Deficient Adenoviral Vectors, 90 Circulation 2414-2424 (Nov. 1994).

Mulhauser et al., Safety and Efficacy of In Vivo Gene Transfer into the Porcine Heart with Replication-deficient, Recombinant Adenovirus Vectors, 3 Gene Therapy 145-153 (1996).

Putney et al., Improving Protein Therapeutics with Sustained-Release Formulations, 16 Nature Biotechnology 153-57 (Feb. 1998).

* cited by examiner

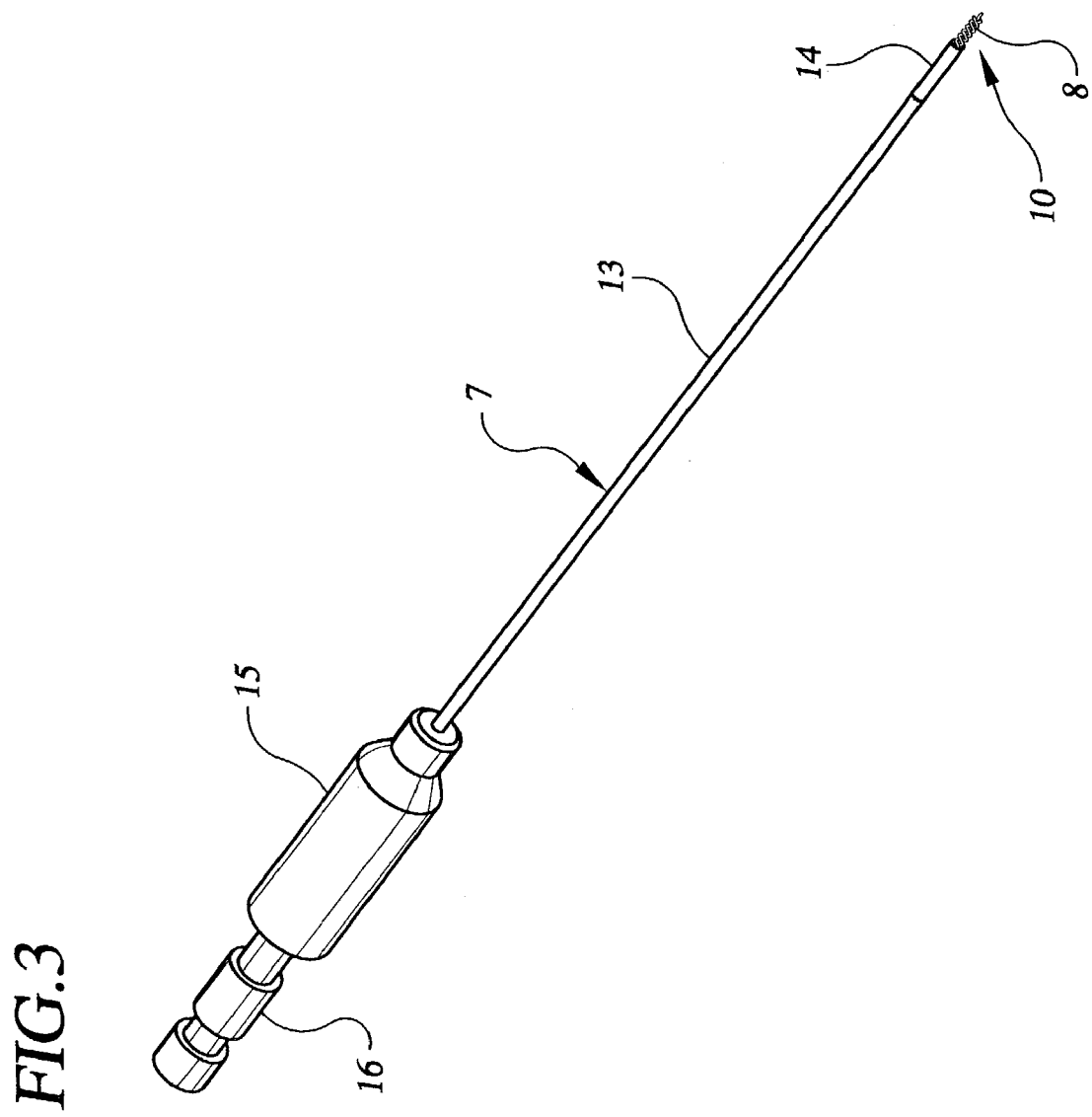

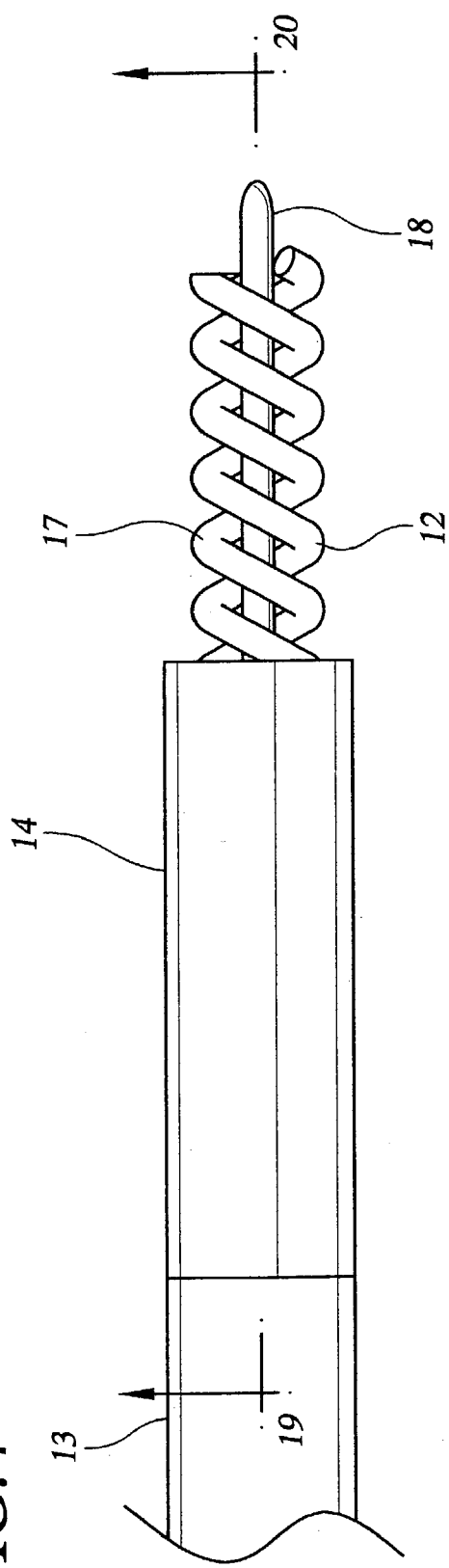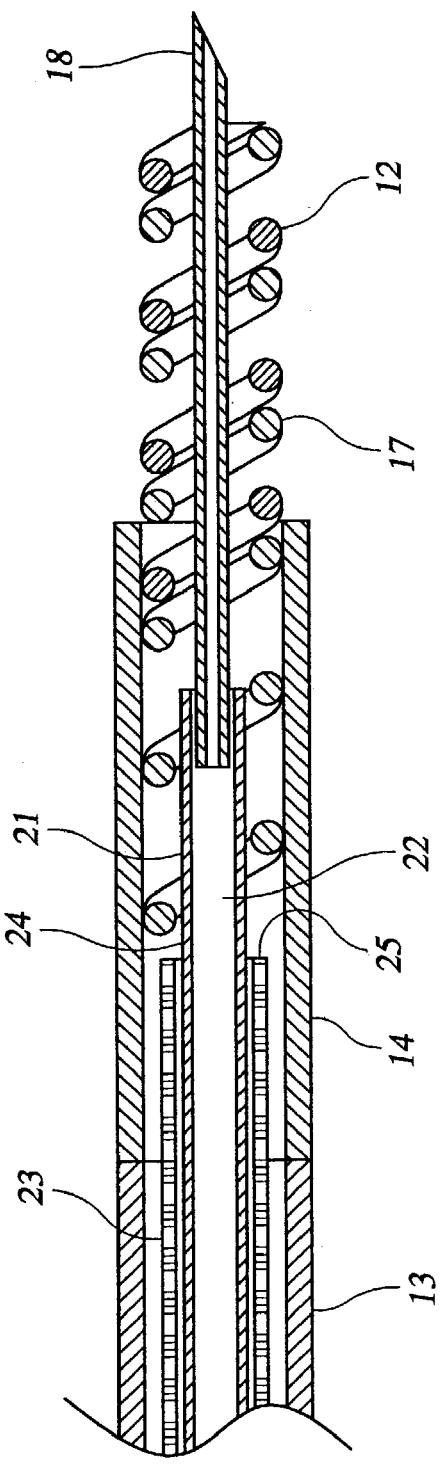

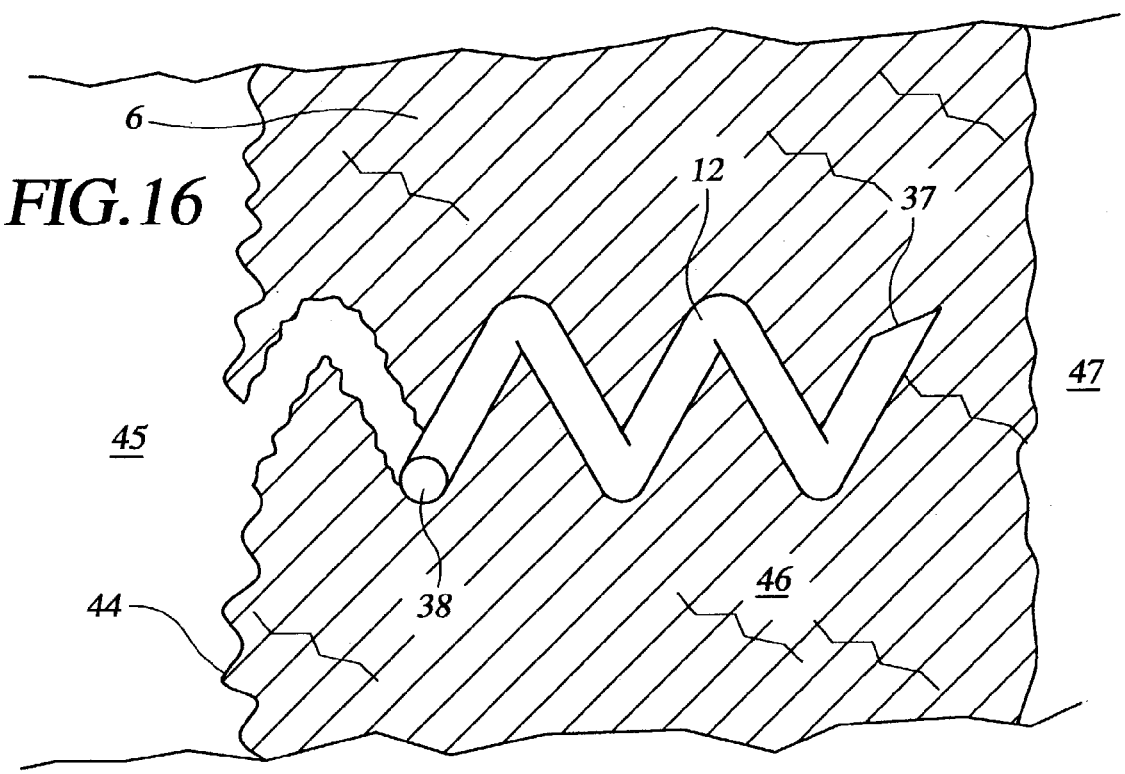
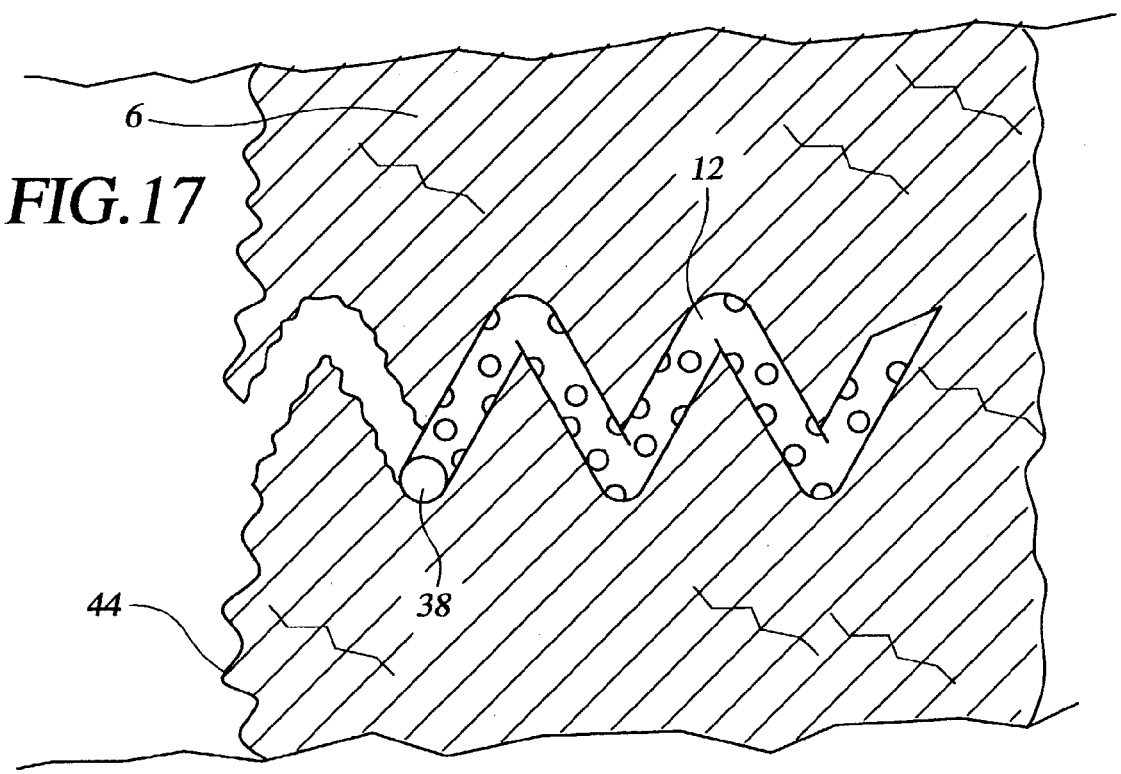

IMPLANT DELIVERY CATHETER SYSTEM AND METHODS FOR ITS USE

This application is a continuation of U.S. patent application Ser. No. 09/543,127 filed Apr. 5, 2000, now U.S. Pat. No. 6,478,776.

FIELD OF THE INVENTIONS

The inventions described below relate to site-specific delivery of therapeutic agents, devices, structures and catheter systems, means for implanting and using these systems to enable delivery of therapeutic agents to the body, and methods for manufacturing these devices.

BACKGROUND OF THE INVENTIONS

Cardiovascular disease is the leading cause of death in the United States and many other developed countries. A major contributing factor to cardiovascular disease is atherosclerosis, or the hardening of the arteries due to plaque formation. As atherosclerosis progresses, the blood vessels narrow and may close entirely. As a result, ischemia, or inadequate blood flow to tissues, can result and damage the affected tissue. In patients with coronary artery disease, ischemia in the heart can lead to severe chest pain, impaired cardiac function or, if very severe, heart attacks. Approximately 50% of deaths attributable to cardiovascular disease are due to coronary artery disease.

Treatment alternatives for coronary artery disease range from risk factor modification and exercise programs for patients with limited disease to major surgical procedures in severely diseased patients. Drug therapy is a mainstay of treatment for coronary artery disease. Surgical intervention such as angioplasty and/or stent placement are often used to open occluded vessels for patients with severe disease. Angioplasty procedures typically use an inflatable balloon catheter to physically open a narrowed blood vessel. Studies have shown that 30% to 40% of the time the artery narrows again, or undergoes restenosis within seven months following angioplasty. The procedure is difficult or impossible to perform on certain patients with multiple vessel disease, diffuse disease, calcified vessels or vessels that are too small to access. Stent placement has become a good alternative to angioplasty, but the challenges of re-occlusion of the stent have not been completely solved, and stents are not generally used to treat multiple occlusions. For patients with severe coronary artery blockages, the preferred treatment is still the coronary artery bypass graft surgery, in which the occluded coronary arteries are replaced with the patient's saphenous vein. The conventional CABG procedure requires cutting through the sternum of the chest and placing the patient on cardiopulmonary bypass, both of which involve significant risk of morbidity and mortality. In addition, it is difficult or impossible to perform CABG on certain patients with diffuse atherosclerotic disease or severe small vessel disease or patients who have previously undergone a CABG procedure.

Pacemakers provide another treatment for heart disease. Pacemakers with helical tipped active fixation leads have been in clinical use for greater than 25 years. Often when implantable leads become infected or fail due to fatigue, physicians will extract the entire body of the lead and leave behind the active fixation element which is buried in the myocardium. Furman S.; Hayes, D.; Holmes, D.: *A Practice of Cardiac Pacing*, Futura, Mount Kisco, N.Y., 3$^{rd}$ ed., 1993 shows an image of a patient with four separate abandoned intramyocardial electrodes in addition to two more additional electrodes for dual chamber pacing left behind in the heart with no apparent effect. It is well recognized that a helical intramyocardial implant remnant resulting from the extraction of a lead system poses no known risk to the patient.

Restoring blood flow to areas of ischemia through angiogenesis offers one of the most promising therapeutic options for treatment of coronary artery disease. Angiogenesis, or the formation of new blood vessels, is the body's natural response to ischemia. It also occurs as a normal physiological process during periods of tissue growth, such as an increase in muscle or fat, during the menstrual cycle and pregnancy, and during healing of wounds. Under ischemic conditions, expression of certain genes leads to the production of growth factors and other proteins involved in angiogenesis. The endothelial cells, which line blood vessels, contain receptors that bind to growth factors. Binding of the growth factors to these receptors triggers a complex series of events, including the replication and migration of endothelial cells to ischemic sites, as well as their formation into new blood vessels. However, in ischemic conditions, the growth factor genes often may not produce sufficient amounts of the corresponding proteins to generate an adequate number of new blood vessels. A logical therapeutic approach to this problem is to enhance the body's own response by temporarily providing higher concentrations of growth factors at the disease site. For cardiac disease, this will require a cardiovascular delivery system. Current delivery systems however are undesirable for a number of reasons.

One delivery system that has been proposed is the delivery of angiogenic agents through the coronary arteries. However, the extent of collateralization (growth of blood vessels elsewhere in the body, like the brain and lenses of the eye) observed is undesirable, so the dose provided must be less than desired. Delivery of recombinant growth factors bFGF and VEGF to the coronary arteries has entered Phase II human clinical trials, but the route of administration does not appear to be optimal. This is best shown by the recently completed VIVA phase II clinical trial in which rhVEGF 165 was delivered to both the coronary arteries and intravenously over periods of time, and yet did not show a statistically significant improvement in the patients who received the drug versus the placebo.

Additionally, arterial delivery treats the tissue subtended by the vessel with agents delivered to the most highly perfused tissue and rapidly washing away from the tissue. If agents are delivered to the coronary artery, the coronary artery bed, which includes richly and poorly perfused regions, will receive the drug therapy. Due to the nature of the restenosis or flow restriction, poorly perfused (ischemic) areas will receive less angiogenic agents, and healthy tissue will receive more. As the underlying problem of ischemic tissue is poor perfusion, excess growth factor must be delivered in order to obtain the desired effects in the poorly perfused tissue. Because of the high flow in the arteries, growth factor that is not bound by receptors in the vessels is quickly distributed to the rest of the body.

The pharmacokinetics of these clinical studies has not been discussed scientifically, yet it has been shown that sustained delivery is important to promote optimal angiogenesis. Gene therapy preparations are being used in the clinic to provide for sustained delivery of different forms of angiogenic agents VEGF and FGF to increase the magnitude of the therapeutic effect. Gene therapy currently suffers the difficulty that agents must be (1) delivered to the site, (2)

gain access to the targeted cell cytosol, (3) become incorporated in the host cell's DNA, (4) be transcribed to produce mRNA, (5) the mRNA must be translated to produce the protein, and then (6) the protein must find a means of egress from the cytosol to the extracellular space in order to have its intended endogenous effects of promoting angiogenesis. At each of these six steps there are substantial efficiency issues that are difficult to control. There are currently three clinical trials entering Phase II studies in which the effective dose (step 6 of the cascade) of therapeutic protein that is being delivered to the tissue is not well understood.

Implantation of local drug delivery depots is an alternative to poorly controllable injection of gene therapy preparations. However, currently proposed depots pose difficulties. The processing steps needed to make them can render the therapeutic agent to be delivered biologically inactive. Nugent, M. A., Chen O. S., and Edelman, E. R., Controlled release of fibroblast growth factor: activity in cell culture. 252 Mat. Res. Soc. Symp. Proc.: 273 (1992) illustrates the difficulties in producing useful depots. They identified the problem with Ethylene Vinyl Acetate Copolymer (EVAC) delivery of bFGF as being attributable to the denaturation of nearly 95% of the protein by the organic solvents necessary to fabricate EVAC matrices. This means that for a desired dose, about 20 times the desired dose must be used to end up with an implant that carries the desired dose. Recently, these issues have been resolved for surgical delivery of bFGF by the successful surgical implantation through the epicardium of alginate encapsulated heparin sepharose controlled release depots in a phase I clinical trial. Sellke, et a;. Therapeutic Angiogenesis with Basic Fibroblast Growth Factor: Technique and Early Results, 65 Annals Thoracic Surgery, 1540 (1998). Although this is by far the most advanced work done to date, the controlled release depots are too large (0.5 cm to 1.0 cm in diameter) to be delivered percutaneously by a catheter system. Their placement requires surgical access to the surface of the heart. It is also unlikely that the desired target area for these devices is epicardial or even endomyocardial as ischemic zones tend to be localized to the subendocardium. These issues limit this delivery approach, add risks to the patients who receive it, and increase the procedural costs of this delivery method.

Our own catheter systems with helical infusion needles for interstitial delivery provide for delivery of small controlled release structures such as microspheres (diameter=15 to 150 um) by transporting them through a fluid slurry to a depth within the heart with high efficiency. Our system reduces the potential of "back leak" or "squeeze out" of controlled release microsphere slurry or gel materials into the left ventricular chamber. These small controlled release systems have a very large surface-area-to-volume ratio, thus making it difficult to provide optimal release kinetics for many known microsphere systems, such as the Alkermes Prolease system. It can be difficult to achieve zero order release kinetics in which the dose is delivered at a constant rate over time. In addition, polymeric microspheres require formulation specific issues to be addressed for each agent that is to be delivered, and these can cause additional problems as already discussed.

If the drug releasing structure is implanted in the left ventricle from the endocardial surface, there is a danger that solid particles can escape into the arterial blood system and be pumped out to the body. These embolic particles could end up lodged in a vessel and occlude it, causing ischemia or necrosis to tissue elsewhere in the body. Another danger is that a proliferative agent, such as a growth factor, could embolize and be delivered to an unintended area of the body, such as the brain or the retina, where new uncontrolled blood vessel growth (angiogenesis) could damage healthy tissue. Therefore, there is a need for a structure that can deliver solid or degradable forms of therapeutic to a depth of the myocardium while lowering the risk for embolic events.

SUMMARY

The devices and methods described below provide for new treatments for heart disease. The treatment includes permanent placement of a drug-carrying coil or dart into the center of the myocardium, isolated from the internal chambers of the heart and pericardial space outside the heart. The coil or dart can be pushed into the heart wall from a catheter that is navigated through the patient's arteries and into the patient's heart, so that the device is inserted into the heart wall from inside the heart. The coils and darts are made in various embodiments allowing them to be loaded with a drug which, after implantation, slowly seeps into the heart wall and delivers minute amounts of drugs steadily over several weeks. The device designed to deliver coils includes the coil and comprises a catheter used to deliver the coil and a releasable connector connects the coil to the catheter. In one embodiment, the catheter has a second coil, which we refer to as the fixation coil, securely fixed to the distal end of the catheter. The drug delivery coil nests inside the coils of the fixation coil, and can be helically rotated distally to detach itself from the fixation coil, but the catheter prevents its rotation proximally. Thus, when the surgeon screws the fixation coil into the heart wall, the drug delivery coil is driven in along with the fixation coil, but when the surgeon unscrews the fixation coil from the heart wall, the drug delivery coil remains in place. In an embodiment designed to deliver darts into the heart wall, the catheter includes the fixation coil fixed to the distal tip and the dart releasably attached to the distal tip. The surgeon screws the fixation coil into the heart wall, and then drives the dart into the heart wall through the center of the helix. When the surgeon unscrews the fixation helix from the heart wall, the dart is left behind. Various embodiments of the drug delivery coils and dart are also disclosed, as well as methods for making them.

BRIEF DESCRIPTION OF THE DRAWINGS

FIG. 3 shows an isometric view of the deployable helix catheter with the sheath retracted and the controlled release structure ready to be deployed.

FIG. 4 is an enlarged view of the distal end of the deployable helix catheter with the sheath covering the distal end partially retracted to expose the dual helices.

FIG. 5 is an enlarged cross sectional view of the distal end of the deployable helix catheter with the sheath retracted and the controlled release structure ready to be deployed.

FIG. 16 is a schematic and cross-sectional view of a helically shaped controlled release structure embedded in the wall of the myocardium, to a depth within the myocardium.

FIG. 17 is a schematic and cross-sectional view of an alternately constructed helically shaped controlled release structure embedded in the wall of the myocardium to a depth within the myocardium

DETAILED DESCRIPTION OF THE INVENTIONS

Figure 1:
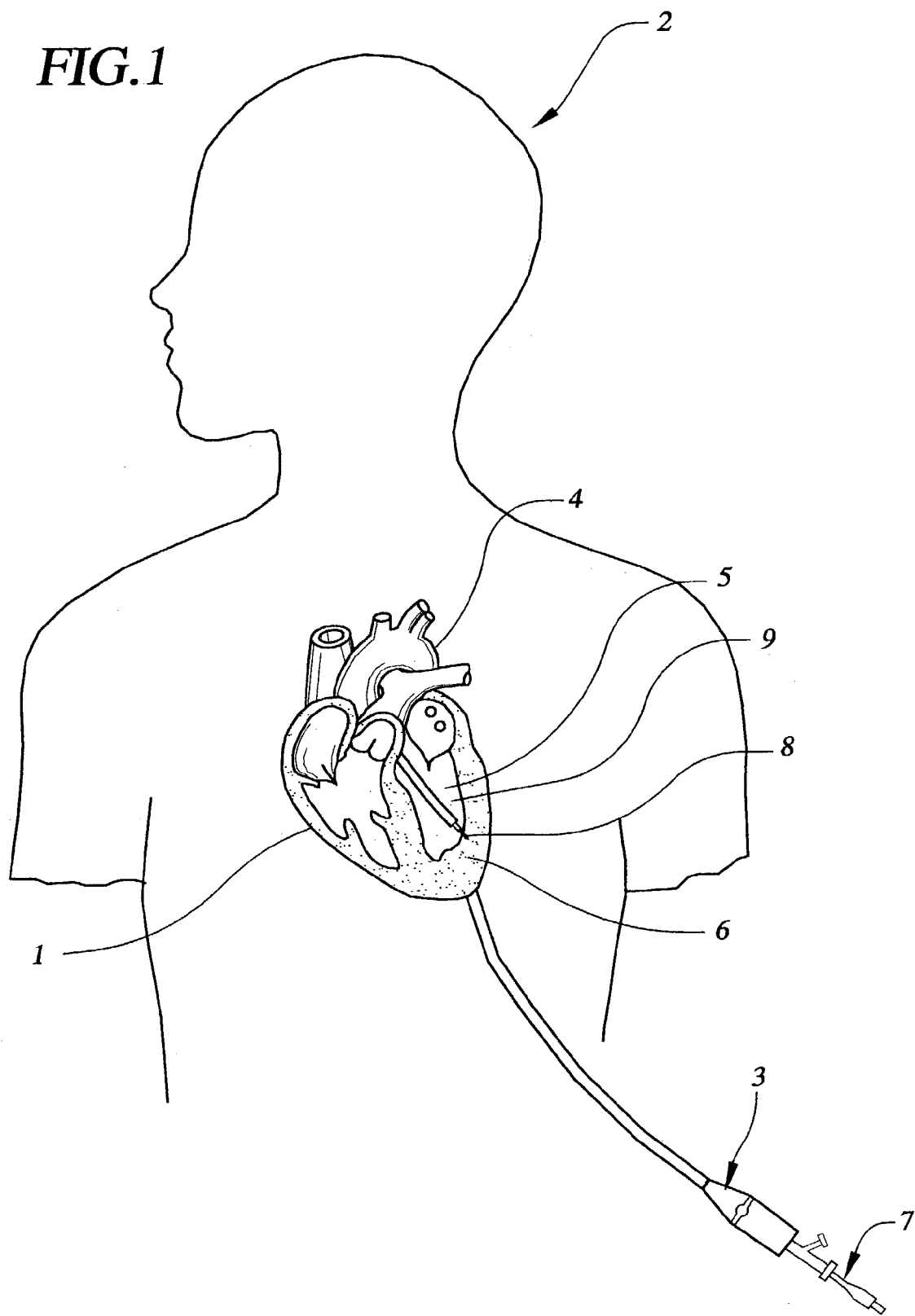
FIG. 1 shows a sectional view of a patient's heart with an implant delivery catheter with a deployable element placed through a guide catheter into the left ventricle wall.

FIG. 1 shows a sectional view of the heart 1 within a patient 2. A steerable guide catheter system 3 is placed within the patient, having been percutaneously inserted into an artery such as the femoral artery, and passed retrograde across the aorta 4 and into the left ventricular chamber 5. Steerable guide catheter 3 is advanced through the patient's vasculature into the left ventricle in order to target a region of the heart wall 6 for delivery. An implant delivery catheter 7 with a fixation element 8 has been inserted through the guide catheter, so that the distal tip of the implant delivery catheter and the fixation element are proximate the target region of the heart. Once oriented toward a region of the heart wall 6 within, for example, the left ventricle wall 9, the centrally located implant delivery catheter 7 is advanced into the heart wall 9 and fixed to the heart tissue by means of the fixation element 8. As described below, the catheter shown in FIG. 1 is different from the prior art in that it can deliver a helically shaped controlled release drug reservoir to a depth within the intended tissue, so that the reservoir is below the surface of the tissue.

Figure 2:
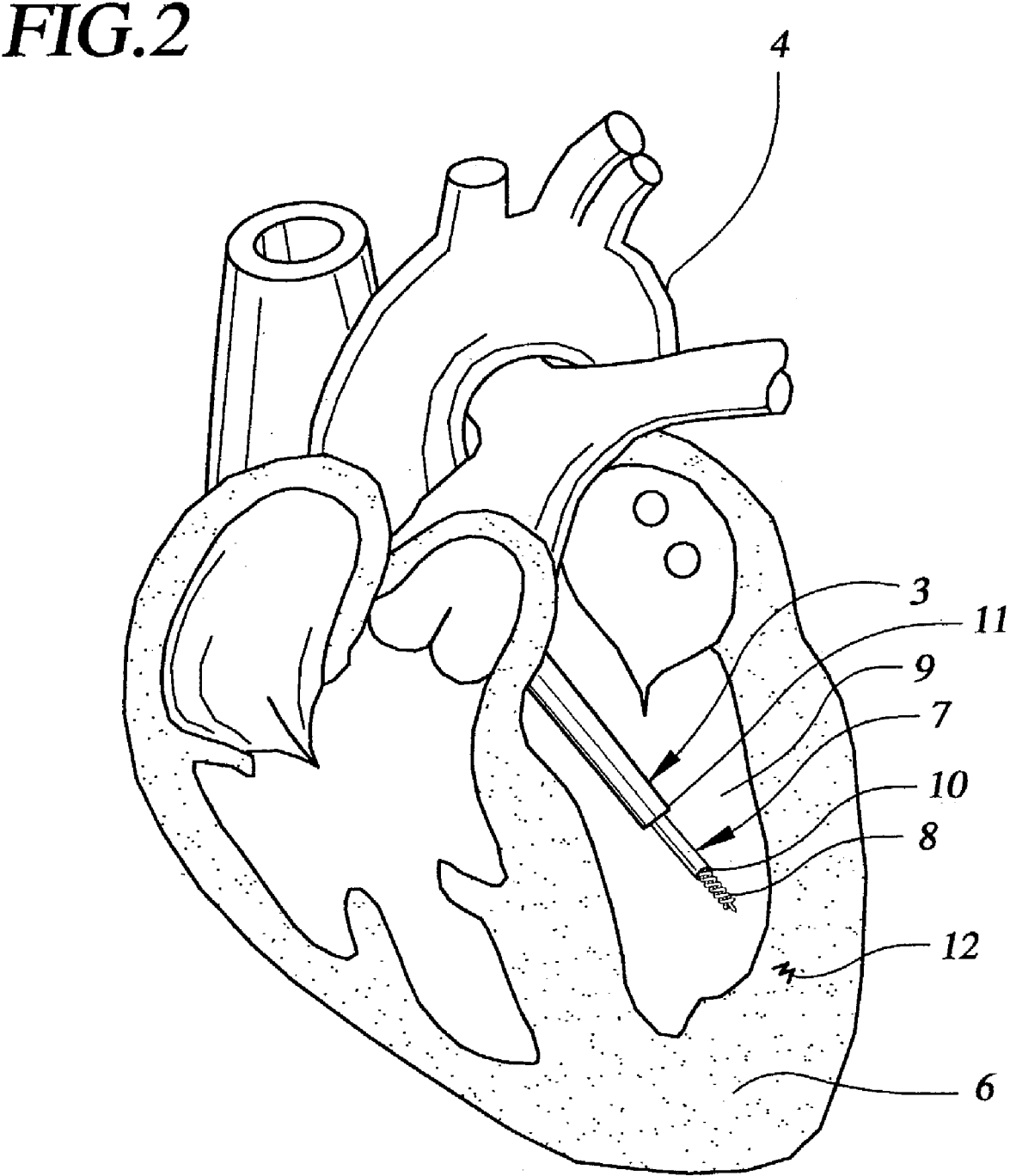
FIG. 2 shows an enlarged view of the patient's heart in section, with the implant delivery catheter in the left ventricle, and the helical drug delivery structure implanted in the left ventricle wall.

FIG. 2 shows an enlarged view of the patient's heart with the distal end 10 of the implant delivery catheter 7 and the distal end 11 of the guide catheter 3 within the left ventricle chamber. The surgeon has deployed the helical drug delivery structure 12 into the wall of the left ventricle 9. The implant delivery catheter resides within a lumen of the guide catheter, and is rotatable within the guide catheter. To place the helical drug delivery structure 12 into the myocardium, the surgeon has rotated the implant delivery catheter 7 to screw it into the myocardium. After the drug delivery helix is screwed into the heart wall, the helix is left in place. If the helix is comprised of metal or other non-biodegradeable material, it may remain in place permanently, allowing the drugs carried by the helix to have their desired effect on the heart, while the metal portions of the helix remain in place without harm to the patient. The helix may also be made of a rigid biodegradable material such as polyurethane as described in Leong, U.S. Pat. No. 5,167,907 (Jan. 5, 1993).

As shown in FIG. 3, the implant delivery catheter 7 comprises an outer sheath 13 that slides over an inner core 14 and the tip of the device in the distal tip area 10. The outer sheath is connected to proximal handle 15 and may include braided reinforcement. The fixation element 8, which in this case is a helix or corkscrew with a sharp tip is mounted at the distal tip of the implant delivery catheter, and is operably connected to the proximal handle 16 through the inner core 14. (The outer sheath, though desirable, may be dispensed with, and the guide catheter alone may be used to protect the vascular access pathway from injury due to rotation of the inner core. The implant delivery catheter may be a non-steerable catheter within a steerable guide catheter.

In a third embodiment, a single steerable implant delivery catheter is used, which also allows for deployment of a distally located penetrating structure such as helix 8 shown in FIG. 3 with or without a guide catheter. In a fourth embodiment, the single catheter system may be preformed to effect a particular shape within the heart, while allowing deployment of the distally located penetrating structure which is directed to the desired site in the heart by the preformed shape of the preformed distal tip of the implant delivery catheter. In a fifth embodiment, a dual catheter system is used in which the guide catheter is pre-shaped to effect delivery to a certain location, and the implant delivery catheter is delivered from within the pre-shaped system. The preformed shapes are chosen to facilitate preferred orientation of the distal tip of the catheter system in apposition to a desired site of treatment when the catheter distal tip is at rest within the heart. A sixth embodiment uses a trans-septal approach to the left side of the heart from the right side of the heart. In this embodiment, the guide catheter is routed up the venous side of the patient's vasculature to the right atrium or ventricle. Then a septal crossing device, such as a Brockenbrough needle is used to cross into the left side of the heart through the septum. The helix-deploying catheter is then guided into the left side of the heart within this guide catheter. A seventh embodiment enters the heart through the coronary sinus and delivers the deployable helix from the coronary veins into the myocardium. An eighth embodiment approaches the heart from a transthoracic direction, through the chest wall. In this embodiment, the deployment device is shortened and stiffened so that it reaches the heart through the small spaces between the chest ribs and is stiff enough to support its own weight and the stresses of being passed between the ribs. Of course standard transvascular techniques could be used to implant the device in the right ventricle and the right atria of the heart as well.

FIG. 4 shows a detailed side view of the distal end of the drug delivery structure catheter. The sheath 13 is shown in the pulled back position so that it reveals two helical structures. The anchoring helix 17 is securely fastened to the implant delivery catheter and the inner core 14 so that it rotates with the core when the core is rotated by the operator. The deployable helical drug delivery structure 12 is releasably secured to the catheter inner core such that after it is screwed into the myocardium, it may be released from the inner core and remain in place. The two helices are wrapped in parallel around a common longitudinal axis that coincides with the longitudinal axis of the catheter inner core. A centrally located hollow straight needle 18 is extended through the central axis of the helices and penetrates the myocardium when the helices are screwed in.

FIG. 5 is a cross sectional view of the detailed view in FIG. 4 showing more of the internal details in the catheter. The centrally located hollow straight needle 18 is constructed of sharpened stainless steel. The proximal winds of the helix are wrapped coaxially around the distal tip of the catheter inner core 14 and attached securely by gluing, crimping, heat shrinking or other bonding technologies. The catheter inner core has an infusion tube 21 with a lumen 22 aligned in fluid communication with the lumen of the needle 18. The infusion tube 21 is typically thin walled FEP, PTFE, Pebax, PEO, polyethylene, polyolefin, nylon, or other polymer material that can contain a fluid. The proximal end of the infusion tube 21 is bonded to the proximal handle 16 (shown in FIG. 3) through gluing or other joinery. This creates a fluid path from the proximal handle 16 to the distal straight needle 18 that can be used by the physician to infuse diagnostic or therapeutic fluids during the procedure. The infusion tube is located within the torque transmitting rotational drive shaft 23. The torque transmitting shaft may be separate from the infusion tube or integral with the infusion tube. The extreme distal tip 24 of the torque transmitting shaft forms, with the infusion tube, a distally facing shoulder 25 or protuberance which prevents proximal movement of the helically rotatable drug delivery structure. (Clearly, the rotational drive shaft and the infusion tube can be provided as a single piece, providing a unitary inner core. In this case, an annular flange, boss or protuberance on the inner core will act as the shoulder to prevent proximal movement of the helical drug delivery structure.) The centrally located straight needle 18 also serves to constrain the helical drug delivery structure 12 to the fixed helical anchoring structure 17 during use of the device. The sharp point of the straight needle 18 serves to pierce the tissue and center the device in the myocardium while the operator rotates the helices into the tissue. The fixed helical anchoring structure is attached to the infusion tubing 21, but can be attached to the rotational drive shaft 23. The drive shaft 23 is designed to be flexible in bending but able to transmit torque in either clockwise or counterclockwise directions. The torque transmitting shaft may of various designs of available torque transmitting shafts, including braided shafts, cross-wound drive shafts and coil-reinforced tubing. The reinforcement typically increases the shaft's ability to transmit torque while not significantly increasing it's bending stiffness. The proximal end of the rotational drive shaft 23 is bonded into the proximal handle 16. The proximal handle 16 transmits torque, tension, and compression to the distal fixed helical anchoring structure 17 through this drive shaft 23. The sheath 13 is sized so that it can slide longitudinally over the fixed and helical drug delivery structure 12 and 17 by a clearance or slight friction fit. The sheath material is typically a 35 D durometer soft Pebax polymer. It may be provided with radiopaque loading agents such as barium sulfate or a platinum iridium marker band to make the end of the catheter more evident on x-ray fluoroscopy. This sheath is heat fused to the catheter outer sheath proximal segment 26. The catheter outer sheath proximal segment 26 is typically a braided or reinforced Pebax polymer of varying durometers, usually between 72 D and 40 D. The proximal end of the proximal segment 26 is bonded to the sheath distal handle 15 (shown in FIG. 3) such that when the distal handle 15 is longitudinally translated relative to the catheter inner core handle 16 by the operator, the sheath covers or uncovers the distal parts of the catheter including the fixed anchoring helix 17, deployable helical drug delivery structure 12 and straight hollow needle 18. The sheath 13 and outer shaft 26 are sized to provide a clearance fit over the torque transmission drive shaft 23.

Figure 6:
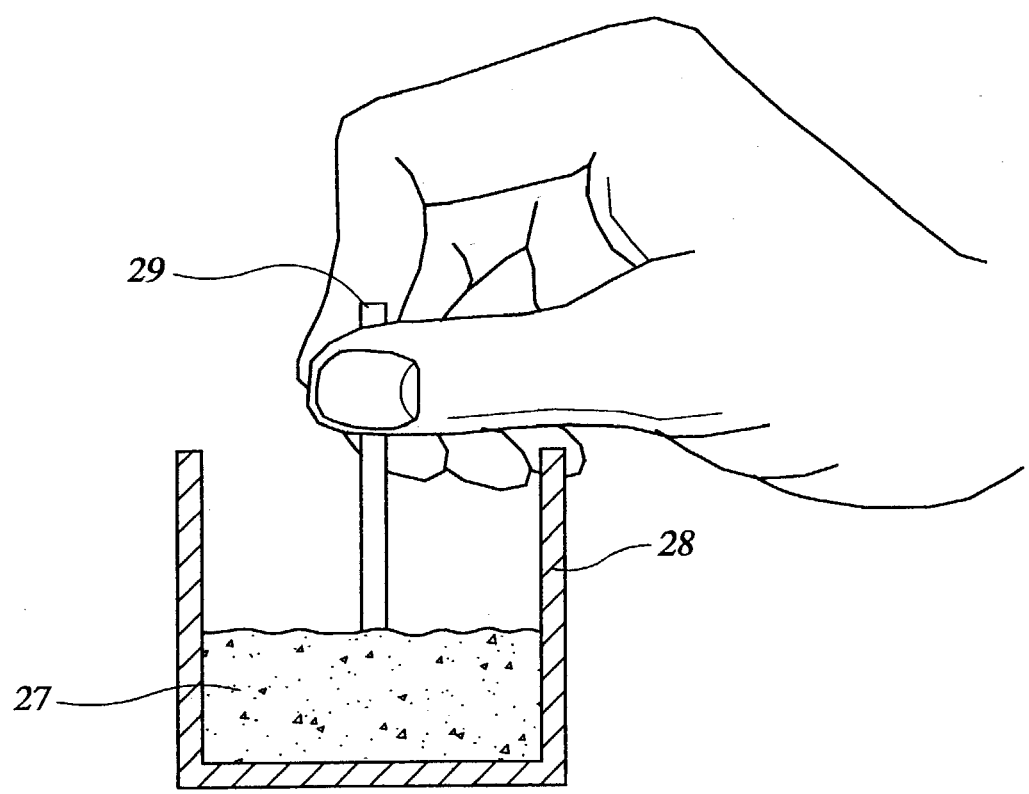
FIG. 6 is a schematic of the tamping method used to incorporate solid therapeutic material into the drug delivery depot tube, prior to creating the drug delivery structure.

FIG. 6 shows one method of filling the hollow implantable tubing with a powdered therapeutic with or without excipients or fillers such as dextrum by tamping the tube into a reservoir of therapeutic agent (the tubing is later wound into the deployable helical drug delivery structure shown in the previous figures). The method may be accomplished by hand or by machine. A reservoir of powder 27 such as lyophilized protein is held in a container 28 such as a glass beaker. The powder is of such a depth that the hollow stainless steel hypo tube 29 can be submerged for a fraction of its length into the powder. The tube is repeatedly tamped into the powder, driving the powder up the tube where it is held by friction. The tubing typically used in this stage is 0.016 inch outside diameter and 0.008 inch inside diameter implant grade 316L or 316 LVM stainless steel. Once enough therapeutic powder is driven into the tube, the tube is made into the deployable helix structure. The ends of the tube are crimped or capped after the tube has been filled as described. One end of the tube may be sharpened before the tamping stage or after the winding stage. If the tube is provided with perforations or apertures communicating from the lumen of the tube through the wall to the exterior (as shown in FIG. 17, for example), the holes may be covered by a temporary and removable polymer sleeve for filling through tamping and then removed either before winding or before implantation, depending upon the consistency of the packed material. Alternatively, the polymer sleeve that covers the apertures in the tubing before packing could be made of a thin bioerodable or biodegradable material such as a polysaccharide, PVA or other known degradable material that is left in place even after the device has been implanted. This polymer sleeve degrades to expose the apertures for delivery. Additionally, the slots or apertures can be potted or filled with the degradable material without coating the entire helix outer surface with the degradable material.

As the drug delivery coil is essentially stuffed with lyophilized protein powder there is no processing required that is agent specific. No chemical interactions other than those that result from the relevantly gentle mechanical tamping techniques required to fill the device will result. No protein goes into solution, interacts with solvent, or has to go through temperature extremes associated with forming cast controlled release devices or spraying of microspheres. This results in a device that should work well for nearly any lyophilized protein that is stable at storage temperature for an extended period of time and body temperature of 37 degrees for the intended duration of delivery.

This approach should provide an easy method to achieve zero order release kinetics in which there is a constant rate of therapeutic delivery from the implanted depot. Delivery of hydrophobic molecules from a reservoir of lyophilized molecules results in a maximum concentration at the interface between the protein exposed to the surrounding fluid milieu and the fluid milieu itself. This concentration will not change at the interface as the fluid milieu becomes saturated at physiological pH and temperature, as there is a reservoir of protein ready to go into solution. Thus it is the effective surface area of the exposed protein-fluid milieu interface that will govern the rate of device release. Since this surface area is fixed and does not change, and the concentration at the interface does not change for a given protein while the depot is active, the release kinetics are governed entirely by the transport in the milieu adjacent to the interface of the device.

Figure 7:
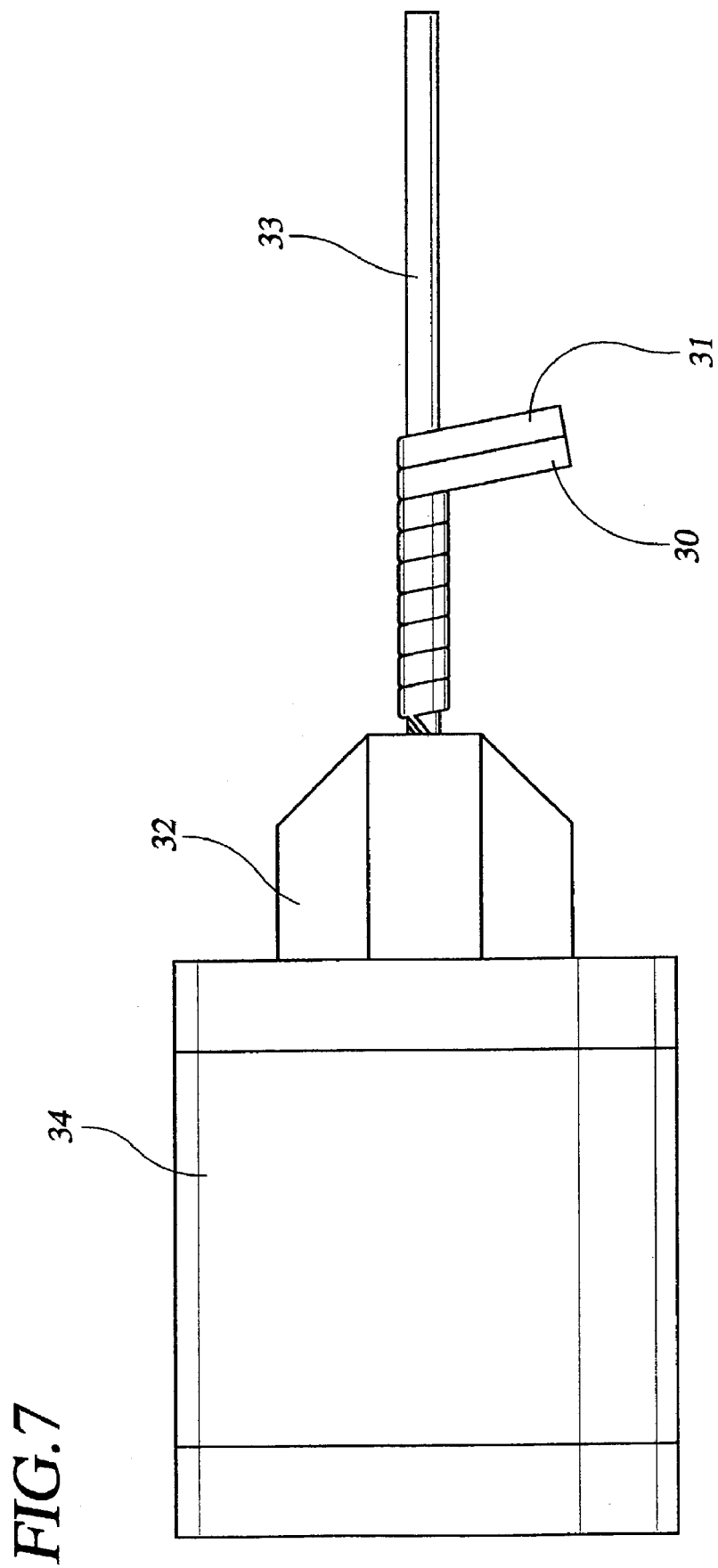
FIG. 7 is a schematic side view of the method used to manufacture the fixed and deployable helical elements of the implant delivery catheter.

FIG. 7 shows an apparatus for winding the fixed and deployable helices used in the construction of the catheter. Two stainless steel tubes or rods 30 and 31 are clamped in a chuck 32 over mandrel 33. The chuck 32 is mounted in block 34. The diameter of mandrel 33 controls the inside pitch diameter of the helices. The stainless steel rods or tubes 30 and 31 are held closely spaced together and at an angle offset from the long axis of the mandrel 33, while chuck 32 is turned either by hand or by an electric motor (one of these rods has preferably been loaded with a therapeutic agent as described above). As the chuck turns, the rods or tubes 30 and 31 are plastically deformed and wound into a helical pattern with the windings of the two helices created arranged parallel to each other and tightly spaced, so that there is little or no gap between the turn of one helix and the surrounding turns of the other helix. The winding spacing controls the pitch of the finished device. When enough length is wound on the mandrel, the chuck is opened and the wound helices are removed from mandrel 33. The helices are then separated, cut to length, and sharpened. One wound helix is bonded into the catheter to become the fixed helical anchoring member, and the other becomes the helical implantable drug delivery structure. Because they are wound at the same time, with the coils touching, they have the same pitch and pitch diameter and therefore nest within one another with a sliding fit. The preferred dimensions of the deployed helical controlled release structure are an outer diameter of between 0.300" and 0.100", with a more preferred range of 0.040" and 0.060". The helix is preferably composed of between 2 and 4 coils, with an inter-coil spacing (pitch) of between 0.020" and 0.060" and a total length of approximately 0.200". The proximal end of the helix is closed. The distal end of the helix is sharpened into a point that easily pierces tissue and remains open to allow the therapeutic agent to diffuse into the tissue. The helix is preferably filled with a volume of between $1 \times 10-5$ cubic centimeters and $9 \times 10-3$ cubic centimeters of therapeutic agent and further preferably around $3 \times 10 \times 4$ cubic centimeters of lyophilized therapeutic agent with or without powdered excipients such as dextrum. The time course of diffusion of therapeutic from a reservoir of this size and length is computed to be on the order of several days depending on molecular size, temperature and diffusion conditions in the tissue in which the structure is placed. The size of the deployable helix and the length of the diffusion path can be modified to shorten or lengthen the path of diffusion as needed for the desired therapeutic.

Figure 8:
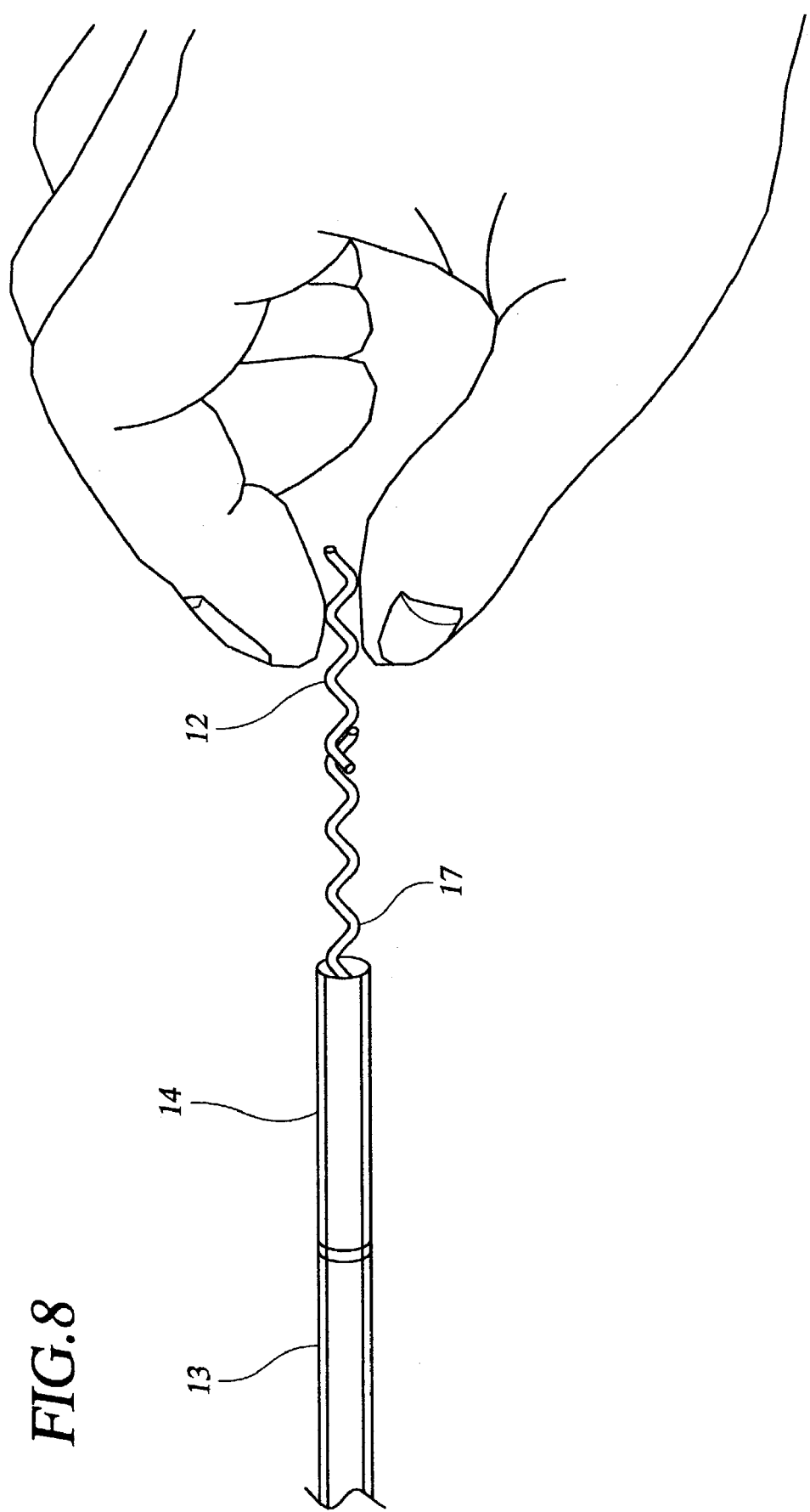
FIG. 8 is a schematic side view of the process of loading the helically shaped deployable controlled release structure onto the distal end of the deploying catheter.

FIG. 8 shows the process of loading the deployable helical drug delivery structure 12 onto the end of the catheter. The loader turns the helical drug delivery structure 12 onto the fixed helical anchoring structure 17 until it is fully seated, having been screwed as far into the catheter sheath 13 as it will go (this will be limited by the distal shoulder of the catheter inner core). When fully seated, the helices are locked together longitudinally and radially (that is, movement along the radius of their radial cross section is not possible), but they may slide along the helical rotational pathway defined by the spaced between successive turns of each helix (and thereby translate longitudinally relative to each other). After seating, the catheter sheath 13 can be advanced to cover both helices by actuating the proximal handles illustrated in the previous figures. The catheter sheath 13 prevents the helical drug delivery structure 12 from working loose of the fixed helical anchoring structure 17 until the device is in use in a patient and operated appropriately by the surgeon. (Not shown in this view is the optional central needle that further stabilizes the two helices and helps with tissue penetration in use. In the preferred embodiment this needle is used.)

Figure 9:
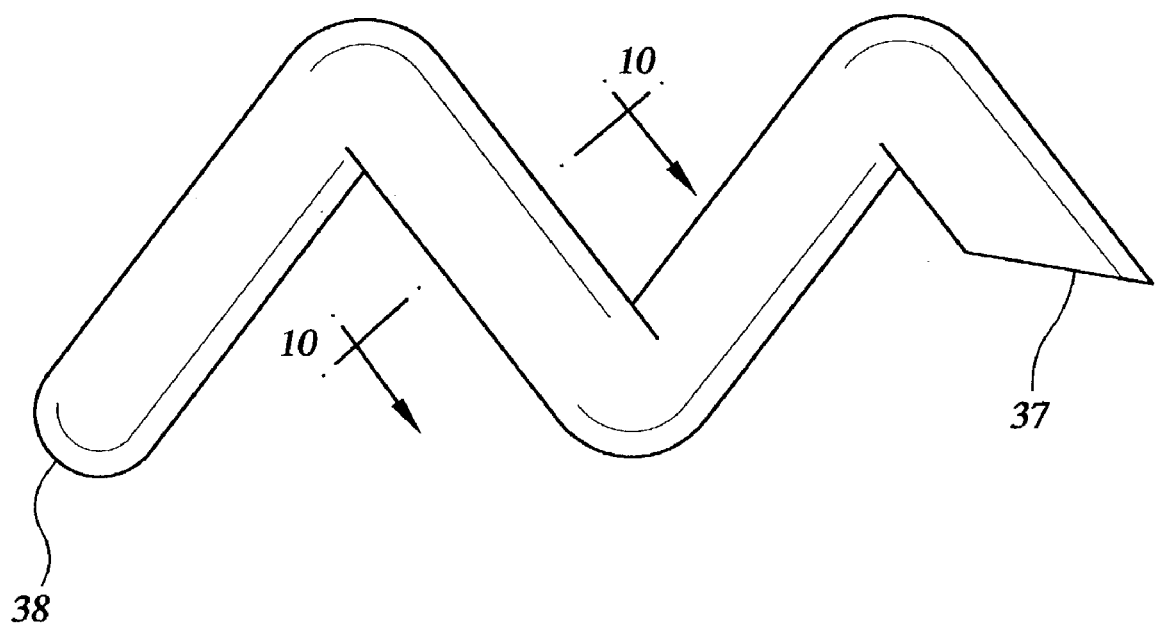
FIG. 9 is a detailed side view of a drug delivery structure that may be deployed by the invention.
Figure 10:
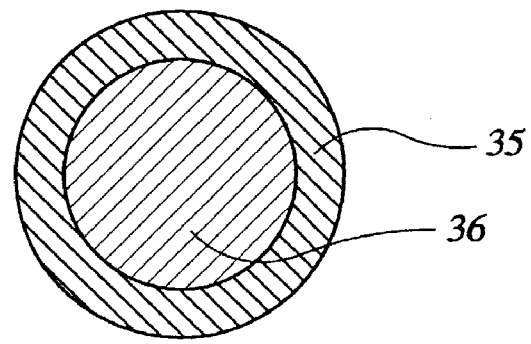
FIG. 10 is a cross sectional view of a drug delivery structure that may be deployed by the invention.

FIG. 9 is a detailed side view of a deployable helical drug delivery structure and FIG. 10 is a cross sectional view of the body of the structure. As illustrated in FIG. 10, the helical drug delivery structure is comprised along its helix length of an outer tube 35 that may be made of an implantable grade stainless steel, platinum, platinum-iridium, polymer, glass or ceramic. The outer tube provides the structural strength for the helix, and includes a lumen within the tube for storage of a therapeutic agent reservoir 36. The distal tip 37 of helical drug delivery structure 12 has been sharpened for tissue penetration. The proximal end 38 of the helical drug delivery structure has been capped with cap 38 to allow only one exit from the reservoir for the therapeutic agent reservoir 39 to escape.

Figure 11:
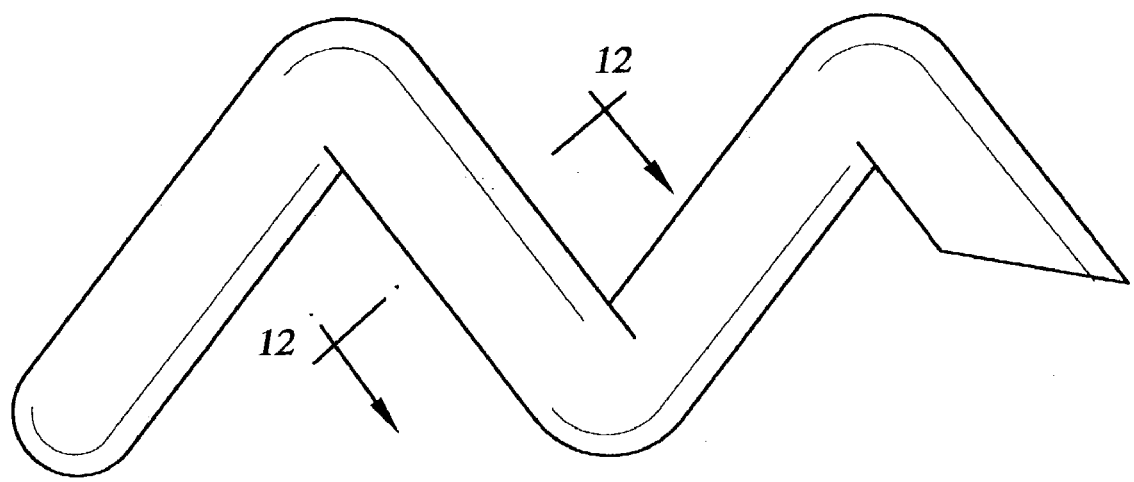
FIG. 11 is a detailed side view of an alternate construction of the drug delivery structure that may be deployed by the invention.
Figure 12:
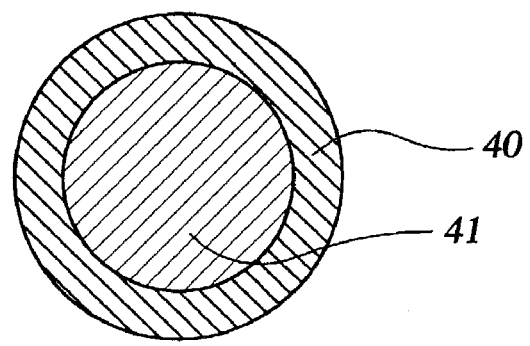
FIG. 12 is a cross sectional of the drug delivery structure of FIG. 11.

FIG. 11 shows an alternative construction for the deployable drug delivery structure. FIG. 12 shows a cross sectional view of the body of the alternative construction. In this construction, the helix comprises a rigid helix coated with an outer coating 40 made up of the therapeutic agent (the therapeutic agent may be encapsulated in a biocompatible polymer controlled release polymer such as EVAC, 1, or a bioabsorbable polymer such as polyurethane). The core material 41 of the helix is the structural element and may be constructed of metal, ceramic, glass, or polymer. The coating is intended to allow the therapeutic agent to leach, dissolve, or degrade into the myocardium to deliver therapeutic agents (although non-degradable agents that remain firmly attached to the core helix may be used). In this embodiment, the therapeutic begins to escape in all directions as soon as the structure is inserted into the tissue.

Figure 13:
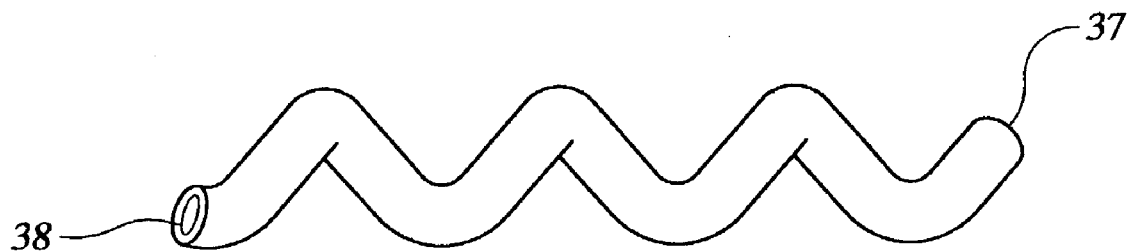
FIGS. 13, 14, and 15 are detailed views of alternate constructions of drug delivery structures that may be deployed by the invention.
Figure 14:
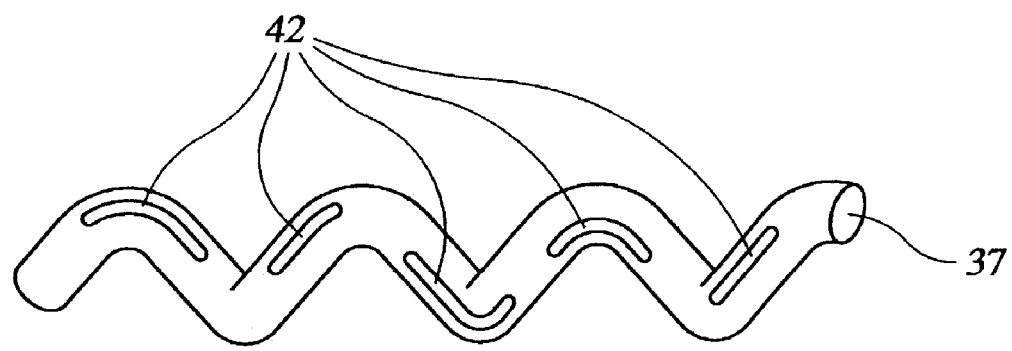
Figure 15:
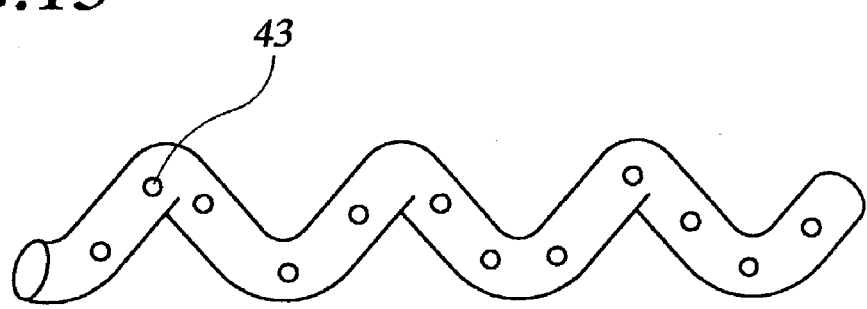

FIGS. 13, 14 and 15 show alternative constructions for the deployable drug delivery structure. In FIG. 13 the proximal end 38 and the distal end 37 of the helical drug delivery structure are both open (the cap 38 shown in FIGS. 9 and 11 is not used). This allows two paths of diffusion for the therapeutic in the center of the device to reach the tissue. In FIG. 14 the helical drug delivery structure has been machined to provide slots or apertures 42 in the wall of the helix, providing for migration of therapeutic agent from the helix over its entire length. In this embodiment, distal end 37 may be closed or open. The slots are sized to allow a controllable rate of drug delivery along the entire length of the helical drug delivery structure. The slots can be created in the helical tube after winding or in the raw material straight tubing used to construct the helix either before or after filling the tube with therapeutic. The slots can be created in the stainless steel tubes by laser cutting, electro-discharge machining, conventional machining, electro-chemical etching or other methods. FIG. 15 shows another construction of the deployable drug delivery structure. This construction has a series of circular holes 43. These holes can be sized and positioned to control the rate of therapeutic diffusion from the structure. These holes can also be created by the machining methods use to construct the structure shown in FIG. 14.

FIG. 16 shows helical drug delivery structure 12 implanted in the myocardium 6 in the left ventricle. The drug delivery structure 12 has been advanced so that its proximal tip 38 is at a depth below the endocardial surface 44. This allows the endocardium to heal over the small helical needle track wound created by turning the device into the tissue. Eventually, the healing response within the myocardium will seal the drug delivery structure off from the circulating blood within the heart chamber (indicated at item 45). In this figure, the drug delivery depot only has one opening on its distal tip 37 that is located in the ischemic target area 46 of the myocardium. The drug delivery structure is placed at a depth within the myocardium, ensuring that the distal tip of the structure does not penetrate all the way through the heart wall and enter the pericardium or pericardial space 47.

FIG. 17 shows the alternative helical drug delivery structure 12, as illustrated in FIG. 15, implanted in the myocardium 6 of the left ventricle. This helical drug delivery structure has multiple holes for faster diffusion of the therapeutic agent into the tissue to be treated. The therapeutic agent will diffuse into the myocardium over the entire length 48 of the helix.

Figure 18:
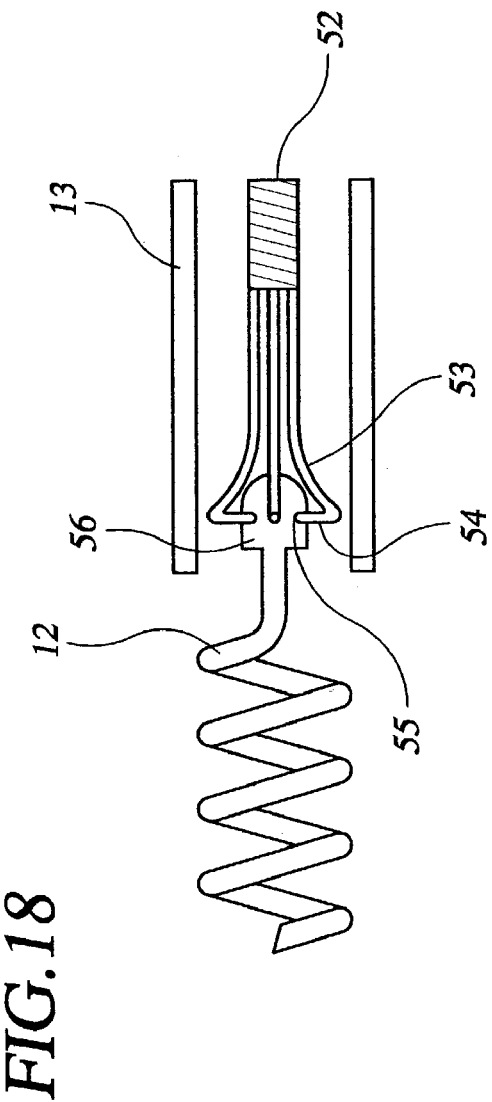
FIGS. 18 and 19 are detailed side views of an alternative method to deploy a helically shaped controlled release structure from a catheter.
Figure 19:
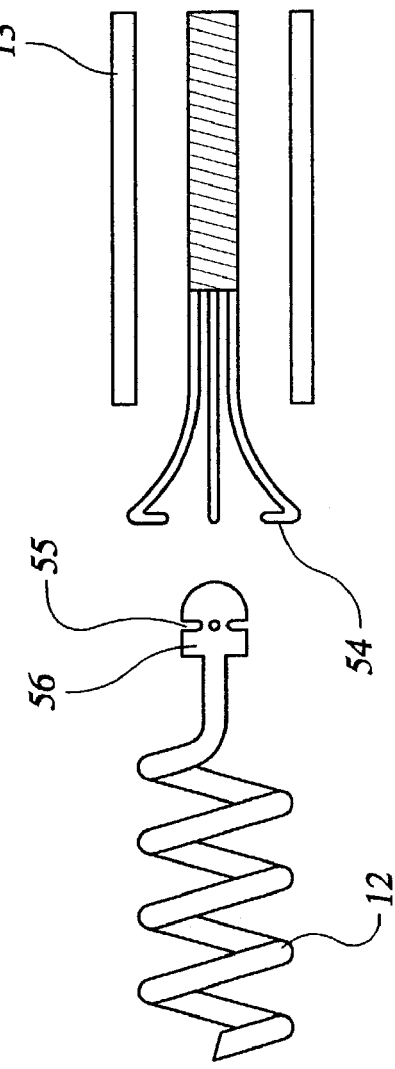

FIG. 18 shows another structure for a delivery catheter distal end and the mating portion of the drug delivery helix. The central holder 52 has resiliently outwardly biased fingers 53 with inwardly facing detents 54 which interact with mating detent receiving ports 55 on the head 56 of the deployable helix 12. In use, after navigation through the vasculature to the target site within the myocardium, the surgeon will first screw the helix into the myocardium to the desired depth, and then retract the catheter outer sheath 13 (that is, slide it proximally) while holding the central holder 52 in place to translate it relative to the holder. (The catheter outer sheath and the inner core are actuated by moving the proximal handles longitudinally relative to one another.) Retraction of the catheter outer sheath allows the spring fingers to open to their open, unrestrained position and release the head of the deployable helix 12 and release the helix from the delivery catheter, as shown in FIG. 19. For removal of the delivery catheter, the proximal handles are operated to retract the central holder 57 into the catheter outer sheath 13, and the outer shaft bends the elastic fingers back to their closed position. The elastic fingers may be formed of resilient material such as 316L stainless steel, spring steel, or shape memory super alloys.

In use, the devices shown in FIGS. 1 and 2 are relatively simple to operate. The surgeon performing the implantation procedure inserts the implant delivery catheter into the patient's vasculature through the skin, typically entering the femoral artery through the thigh, and navigates the catheter into the heart. The surgeon places the distal tip of the catheter, including the fixation coil, in close proximity to the target site within the heart wall, and then rotates the catheter inner core (by turning the proximal handle 16 on the catheter inner core) to screw the fixation coil in to the heart wall. The drug delivery coil, which is nested in the coils of the fixation coil, is forced into the myocardium along with the fixation coil. The surgeon screws the fixation coil into the heart wall until the drug delivery coil is disposed completely within the myocardium, typically ensuring that the proximal tip of the drug delivery coil is below the level of the endocardium, while also ensuring that neither the fixation coil or the drug delivery coil penetrate the heart wall and poke through into the pericardium or pericardial space. When the drug delivery coil is properly located, the surgeon unscrews the fixation coil. The drug delivery coil remains in place within the myocardium because it is not restrained from distal helical rotation relative to the fixation coil. The surgeon may choose to implant a several implants throughout a region of the heart. Thus, the method comprises deploying a series of drug delivery coils loaded with therapeutic agents into the myocardium, and leaving them in place permanently. The therapeutic agents are released over time by diffusion, elution, osmosis, or hydrolysis to have long lasting effect on the heart.

As an adjunct to coil placement, the centrally located hollow straight needle 18 shown in FIGS. 4 and 5 can be used to transiently infuse an additional therapeutic agent to a depth within the heart tissue at the time that the drug delivery coil is implanted. It could also be used to deliver contrast material to confirm penetration of the myocardium. The additional therapeutic agent can be used to ameliorate the immediate effect of the implant, or it can be used to jump start the therapy with a small, quickly absorbable dose of the therapeutic agent or a fast acting analog (that is, having immediate effect relative to the implant). Thus the additional therapeutic agent can be an anti-inflammatory agent, an anti-hypotensive agent, another growth factor or other drug. The transiently delivered fluid agent may start the cascade of healing that the diffusion from the controlled release matrix can continue over time. The transiently delivered fluid could be a heparin binding agent that has a tendency to stick to the interstitial matrix in the myocardium and work over time when given in a single dose. The growth factor in the implanted controlled release matrix could be a non-heparin binding molecule that moves through the interstitial tissue more rapidly, i.e. is easier to clear from the heart, and therefore should be delivered over a period of time.

Figure 20:
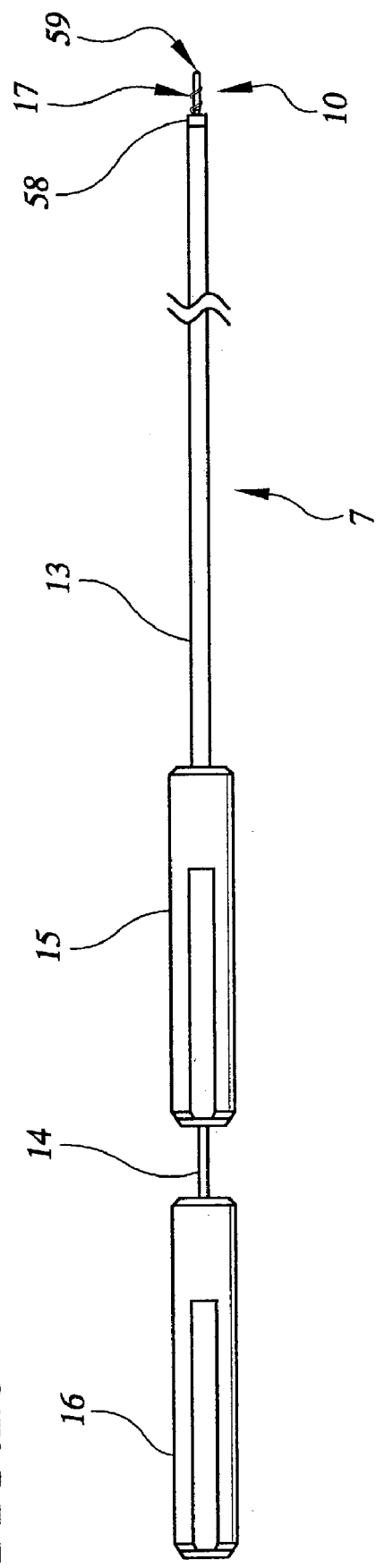
FIG. 20 is a side view of the another deployable drug delivery structure catheter.

FIG. 20 illustrates an embodiment of the implant delivery catheter. The implant delivery catheter 7 comprises the two handles the proximal handle 16 which is secured to the catheter inner core 14 and a distal handle 15 which is secured to the catheter outer sheath 13. The drug delivery dart 59 and anchor helix 17 are disposed on the distal end 10 of the catheter inner core. One or both of the handles has features on it such as ribs or grooves to make gripping more secure or flat on one side so that rotational position can be sensed by feel. The handles can be rotated with respect to one another and can translate longitudinally relative to one another. For the preferred embodiment, the catheter outer sheath 13 is between 0.5 and 3 mm in outer diameter and more preferably between 1 and 2.5 mm in outer diameter. The wall thickness of the catheter outer sheath is between 0.1 and 0.5 mm in thickness. The catheter inner core 14 is preferably between 0.2 and 1 mm in diameter with a wall thickness of 0.1 to 0.3 mm.

Figure 21:
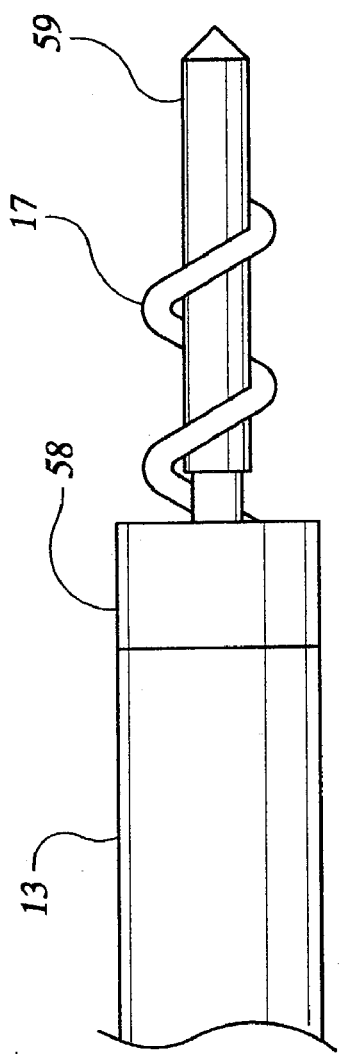
FIG. 21 is a detailed side view of the distal end of the deployable implant delivery catheter in FIG. 20, with the drug delivery structure partially deployed.

FIG. 21 shows the distal end of the catheter shown in FIG. 20. Here catheter outer sheath 13 is shown with distal soft tip 58 with fixation element 8 disposed coaxially around implantable dart 59. Dart 59 may protrude from the catheter outer sheath 13 before insertion into the tissue if so desired, but in its preferred embodiment it is housed in the outer sheath during navigation of the catheter through the vasculature. The dart has a sharpened distal tip 60 to aid tissue penetration and a proximal end 61 with a mating structure for releasably mating with the catheter inner core. The dart is releasably attached to the catheter inner core 14 as illustrated in FIG. 22.

Figure 22:
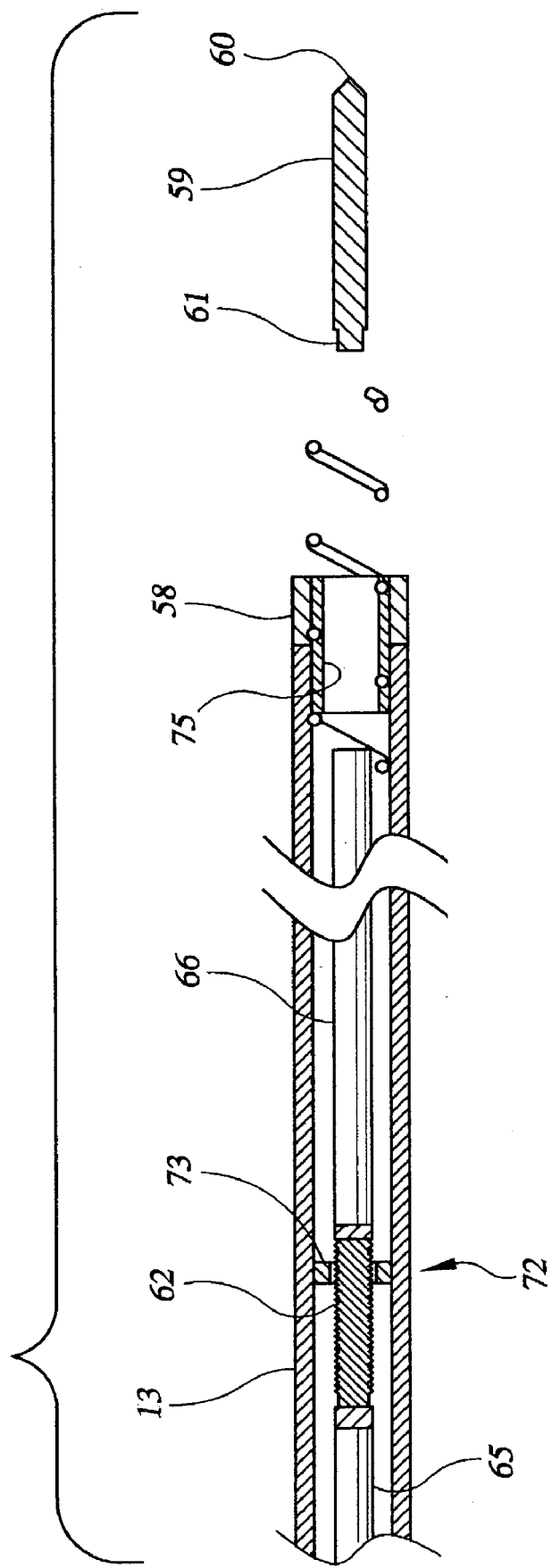
FIG. 22 is a cross sectional of the detailed side view of the distal end of the deployable implant delivery catheter shown in FIG. 21.

FIG. 22 shows a cross sectional view of the distal portion of the catheter shown in FIG. 21. The catheter inner core 14 has a threaded segment 62 located just proximal of the distal tip 63 of the catheter inner core. This segment is fitted with external screw threads 64. This threaded rod portion 64 may be a polymer or metallic rod or tube. The threading is preferably eighty to ninety threads per inch, but can be adjusted to control the amount of travel generated by one rotation. The proximal end of the threaded segment 62 is turned down to a diameter that fits into the distal end of catheter inner core proximal section 65. This joint can be a force fit, or the threaded portion may be glued in with cyanoacrylate, epoxy, or ultraviolet cured adhesives. Alternatively, this joint can be reinforced with an external sheath, heat shrink, crimp or covering. The distal end of the threaded segment 62 is also turned down to a smaller diameter and is inserted into and joined with distal segment 66 of the catheter inner core 14, also constructed of stainless steel braid reinforced polyimide with thin walls. The outer diameter of the distal segment 66 may be the same as the proximal segment 65, or may be larger to more closely match the inside diameter of the catheter outer sheath 13. This portion of distal segment 66 has a distal internal diameter sized to receive the proximal end 61 and mating structure 67 (in this case the necked down area) of the implantable dart 59.

The catheter outer sheath 13 has an internally threaded segment 72 which may be formed with nut embedded at a distance proximal from the distal end and corresponding to the externally threaded segment of the catheter inner core. This nut 73 is internally threaded with the same pitch as the threaded portion 62 of the catheter inner core. The nut 73 is bonded into the internal section of the outer sheath 13 by gluing, crimping, or heat fusing. The distal portion of the catheter inner core proximal section 65 is sized such that it is larger than the opening in nut 73, and the extreme distal tip of the inner core proximal section forms the distal facing shoulder 74 with a diameter exceeding the inner diameter of the nut.

The outer sheath 13 can be composed of one or more sections that are split at the nut location to make assembly easier. The outer sheath portions are heat bonded, glued or welded together after the nut is bonded inside the outer shaft and the drive shaft threaded through the nut. The outer sheath 13 terminates in a soft tip 58 at its distal end. This soft tip is typically 35 durometer Pebax and serves to protect the tissue that the tip of the catheter touches. The soft tip is either heat fused, glued, or otherwise bonded to the end of the remainder of the outer sheath. The soft tip may be loaded with a radiopaque material such as barium sulfate, or have an embedded radiopaque marker band constructed of gold, platinum, platinum/iridium or stainless steel to increase its visibility under x-ray fluoroscopy. Inside the distal part of the outer sheath 13 is the fixation element 8. In this embodiment, the fixation element 8 is a helical structure. This helical structure is made from solid stainless steel rod or hollow wire or tube. The helix is wound such that its outer diameter closely matches the inner diameter of the outer sheath 13. The proximal portion of the helix is preferably encased in a soft Pebax sheath 75. This soft Pebax sheath 75 encapsulation allows the helix to be heat fused with the soft tip 58, making a unitary construction that can transmit torque, tension and compression. This encapsulation sheath 75 may have an internal diameter that is closely mated to the diameter of the dart, to help retain the implantable dart until it is deployed. The fixation element 8 can be constructed of hollow tubing that is connected with a tube that connects up to a luer fitting on the proximal end of the catheter. This tube can be used to inject or infuse diagnostic or therapeutic materials from the proximal end of the catheter to the myocardial tissue in which the catheter is lodged. The fixation element 8 preferably terminates in a sharp point to aid tissue penetration.

In operation, the surgeon first navigates the distal end of the implant delivery catheter through the patients vasculature and in to a heart chamber, so that the dart and fixation element are proximate a target site of heart tissue. The surgeon then rotates the catheter outer sheath while urging it distally, to screw the fixation element into the myocardium. As the fixation element is driven into the myocardium, the surgeon may view the fixation element position to ensure that it is screwed into the desired target site. With the correct positioning ensured, the surgeon rotates the inner core to drive the dart into the myocardium. Rotation of the inner core proximal section 65 turns the threaded segment inside nut 73 and urges the entire catheter inner core forward and drives distal segment 66 forward into the implant dart 59, thereby forcing the dart out of the device. The catheter inner core proximal section 65 may be pulled forward until the distal facing shoulder 74 contacts nut 73 and limits the travel of driveshafts. (Alternatively, this motion can be limited by the distance between the two handles on the proximal end of the device.) This limits the depth to which the dart may be driven, to ensure that it is not driven through the heart wall. The distance 76, which is the distance between the proximal face of the nut (or other inwardly intruding boss on the inner wall of the catheter outer sheath) and the distal face of the shoulder (or other outwardly protruding boss on the catheter inner core) in the ready condition should be chosen such that the maximum possible travel of the dart from the outlet of the catheter is less than the expected thickness of the heart wall.

Figure 23:
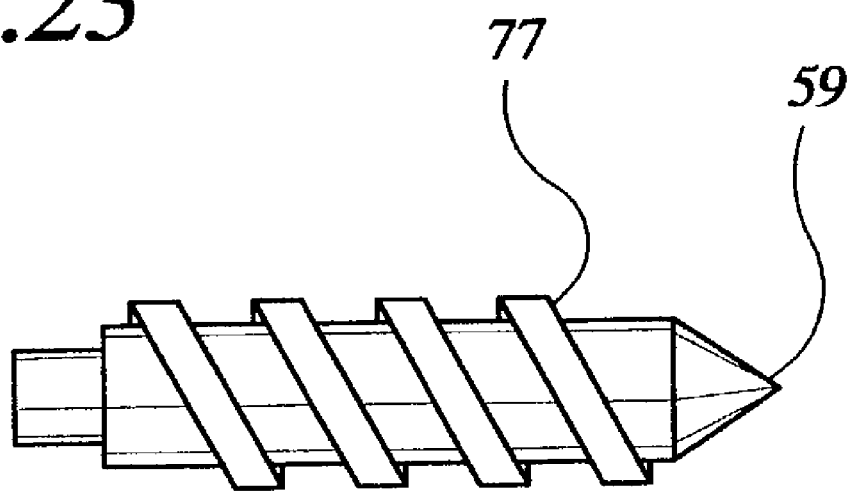
FIGS. 23 and 24 are alternative embodiments of the drug delivery structure.
Figure 24:
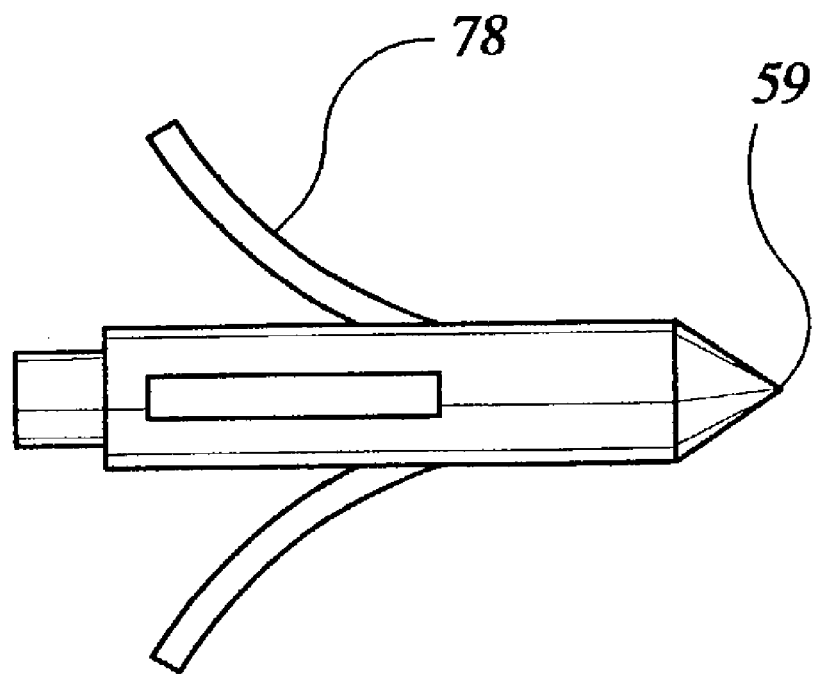
Figure 25:
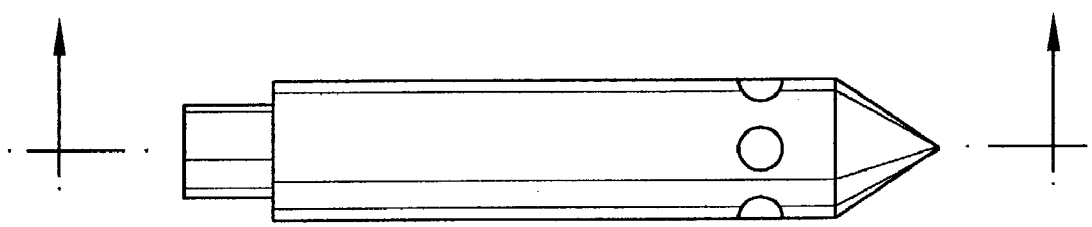
FIG. 25 is a detailed side view of an embodiment of the drug delivery structure that can be delivered by the catheter of this invention.
Figure 26:
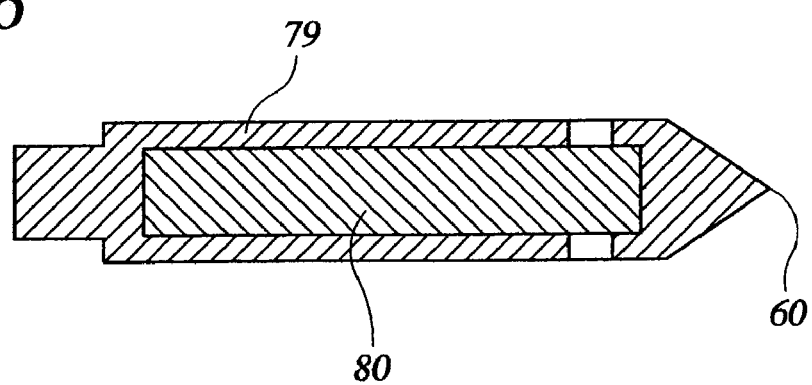
FIG. 26 is a cross sectional view of the drug delivery structure shown in FIG. 25.
Figure 27:
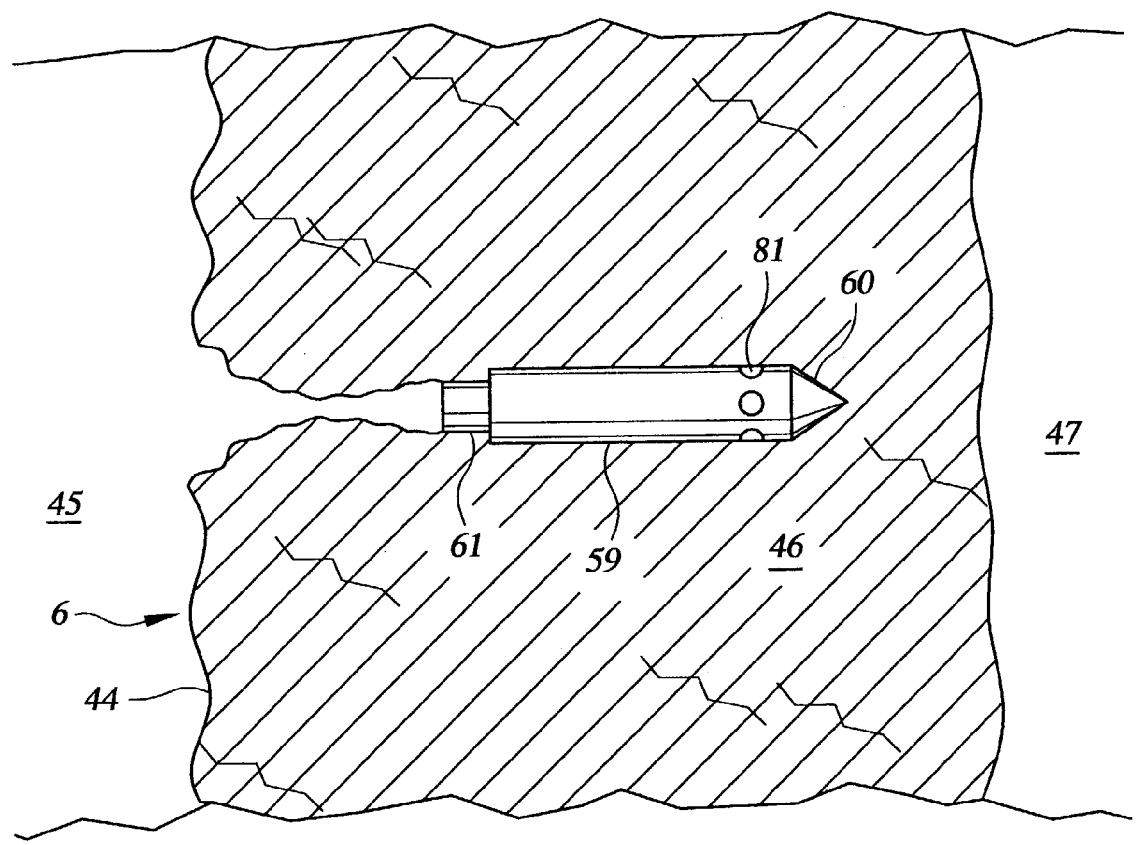
FIG. 27 is a view of the drug delivery structure shown in FIG. 25 embedded in the wall of the myocardium, to a depth within the myocardium.

The dart used in the embodiments of FIG. 22 can be provided in various configurations. As illustrated in FIG. 22, the proximal portion 61 of the dart 59 is turned down to fit into the distal opening in the catheter inner core distal segment 66. The joint is a sliding or loose friction fit between the distal segment shaft and the implant. The dart is constructed of metal, glass, ceramic, polymer or biologic material or a combination thereof. It may or may not have external features to aid its retention in tissue such as barbs, threads or wings. FIG. 23 illustrates the dart 59 fitted with screw threads 77 which enhance retention in the myocardium and increase the surface are of interface between the dart and the myocardium. FIG. 24 illustrates the dart 59 fitted with outwardly biased, radially extending barbs 78 which also enhance retention in the myocardium and increase the surface are of interface between the dart and the myocardium. FIG. 25 shows the dart with a porous or perforated exterior, which may be filled with a fluid therapeutic agent. The porosity or apertures in the exterior permit fluid within the dart to move out of its internal cavity and into the region of the myocardium in which the dart is implanted. The darts may be constructed of a polymer that has been loaded with a therapeutic agent and injection molded into its final form. As shown in FIG. 26, the dart may be constructed of a shell 79 of polymer, ceramic, glass, elastomer and metal that encases a central portion 80 containing therapeutic material such as lyophilized therapeutic protein. The central portion may be a cast, compression molded or extruded reservoir of therapeutic substance or therapeutic substance encapsulated in bioabsorbable polymers or bioabsorbable polymer microspheres. The distal portion 60 of the dart is typically sharpened to a point to ease its insertion into tissue. The point may be multifaceted or conical or beveled. In the preferred embodiment, the diameter of the dart implant is typically 0.5 to 1 mm. The length of the implant is typically 1–10 mm, and more preferably 3–6 mm. The inside edges of the active fixation helix serve to support and guide the implant into the tissue during implantation. FIG. 27 shows the dart-like drug delivery structure implanted in the myocardium 6 in the left ventricle. The drug delivery dart 59 has been advanced so that its proximal end 61 is at a depth below the endocardial surface 44. This allows the endocardium to heal over the small helical needle track wound created by turning the device into the tissue. Eventually, the healing response within the myocardium will seal the drug delivery structure off from the circulating blood within the heart chamber (indicated at item 45). In this figure, the drug delivery depot has several openings 81 on near its distal tip 60 that is located in the ischemic target area 46 of the myocardium. The drug delivery structure is placed at a depth within the myocardium, ensuring that the distal tip of the structure does not penetrate all the way through the heart wall and enter the pericardium or pericardial space 47.

The helix can be loaded with therapeutic agents using many methods. The tubing can be filled with the powder by pouring the powder into the top of the hollow tube through a funnel. This filling process can be aided by agitating the supply or receiving tubes with mechanical or ultrasonic vibration. After filling, one or both ends of the hollow tube may be closed by crimping or capping or plugging. The process may take place in a controlled environment, such as under dry nitrogen gas at 0 degrees Celsius, to keep the protein dry, loose, and stable. The lyophilized protein can be made into a paste or suspension and driven into the hollow helical tube by pressure exerted by a syringe, fluid dispenser, pump, or compressed gas source. The suspension liquid would be non-reactive with the protein and would later be evaporated or driven off by elevated temperature storage. Multiple therapeutic agents can be mixed in their dry form and the mixture can be installed in the controlled release structure. In addition to powdered lyophilized therapeutic, the deployable helix structure can be filled with microspheres that have been loaded with the therapeutic agent. Spheres in diameter up to the inside diameter of the helical tubing can be used, 0.008". These spheres could be constructed of bioabsorbable polymers that bulk erode, bioabsorbable polymers that surface erode, or nonabsorbable biocompatible polymers with diffusion paths and pores depending on the desired time course of elution. Another means of filling the hollow helix or helical tube with therapeutic protein is to dip the tubes into a solution of solvent and therapeutic protein. The tube is then air dried or placed in an oven to drive off the solvent. A coating of therapeutic powder is left behind. This process can be repeated to deposit more therapeutic agent until the desired quantity is achieved. Another means of filling the hollow helical tube with therapeutic agent is to insert mold or overmold the tube or finished helix with a polymer, either bioabsorbable or biocompatible, that has been loaded with the therapeutic. These polymers may be urethanes, polylactides, polyglycolides, polycaprolactones, polyanhydrides, acrylics, polyesters, epoxies and the like. If the therapeutic agent is only stable at low temperatures, this filling or coating can be completed with a low temperature casting material such as urethane, epoxy or acrylic. Another means of filling the hollow helix with therapeutic agent is to cast, mold, or extrude the therapeutic agent and a polymer carrier into a rod or thread form. This thread or rod can be inserted into the hollow helix tube and locked in place before the tube is bent into the helical shape around the mandrel. The fixation may be by a mechanical interference, or crimping, or melting to constrain the thread relative to the tube.

Alternatively, the hollow helix can be filled with the therapeutic agent intraoperatively. If the tube contains a hydrophilic biocompatible polymer core or coating, such as ethylene vinyl acetate copolymer (EVA), the surgeon would dip or soak the deployable helix in a reconstituted solution of therapeutic agent and saline or ringer's lactate. The hydrophilic medium in or around the helix would take up the therapeutic by capillary action and wicking, thereby loading the deployable helix device. Alternatively, the doctor could fill the helix with therapeutic solution by coupling the helix to a syringe and injecting the solution into the lumen of the helix before attaching the helix to the catheter. Another method of constructing a deployable helix is to sinter a metal or ceramic into the final shape. The sintered helix would have a porous construction that could wick up the therapeutic fluid through capillary action as described above.

While the devices and methods have been described in relation to the treatment of the heart and treatments for ischemia with implantation of a helix or dart loaded with an angiogenic agent, they may be adapted to treat other conditions within the heart, other organs of the body, and conditions such as tumor and cancers. For example, the coils or darts or implants of other shapes can be adapted for implant into a tumor and loaded with a tumor necrosis factor. Many compounds may be loaded into the implants. "Angiogenic agents" and "endothelial agents" including the following may be used: insulin like growth factor-I (IGF-I), VEGF, VIGF, PDGF, epidermal growth factor (EGF), CTGF and members of its family, FGF, TGF-a and TGF B; the widely recognized angiogenic agents VEGF-165, VEGF-121, VEGF-145, FGF-1, FGF-2, Transforming Growth Factor (TGF-B), Tumor Necrosis Factor a (TNF-a), Tumor Necrosis Factor B (TNF-B), Angiogenin, Interleukin-8, Proliferin, Prostaglandins (PGE), Placental Growth factor, Granulocyte Growth Factor, Platelet Derived Endothelial Cell Growth Factor, Hepatocyte Growth Factor, DEL-1, Angiostatin-1 and Pleiotrophin.

For treatment of cancers and tumors, angiostatic agents may be used including antibodies or other antagonists to angiogenic agents as defined above, such as antibodies to VEGF or Angiotensin 2 and cytotherapeutic agents such as cytotoxic agents, chemotherapeutic agents, growth inhibitory agents, apoptotic agents, and other agents to treat cancer, such as anti-HER-2, anti CD20, paclitaxel, cisplatin, and other bioactive and organic chemical agents.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A method of delivering a therapeutic agent to a depth within the myocardium, said method comprising steps of:
   providing a tube;
   filling the lumen of the tube with a therapeutic agent by tamping an open end of the tube into a reservoir of therapeutic agent;
   forming the tube into a helical coil;
   covering the tube with a sleeve;
   twisting the helical coil so that it penetrates the endocardium, thereby driving the helical tube into the endocardium; and
   leaving the helical tube implanted in the endocardium and permitting the therapeutic agent to transit from lumen of the helical tube to the endocardium over time.

2. The method of claim 1 further comprising the step of:
   providing the therapeutic agent in the form of lyophilized protein powder, macromolecules, gene therapy preparations, microspheres, or micelles.

3. The method of claim 1 further comprising the step of:
   filling the lumen of the tube with a biodegradable polymer loaded with the therapeutic agent.

\* \* \* \* \*